(12) United States Patent
Kübler et al.

(10) Patent No.: US 12,728,124 B2
(45) Date of Patent: Sep. 8, 2026

(54) MEDICAL USE OF CYSTIC FIBROSIS TRANSMEMBRANE CONDUCTANCE REGULATOR (CFTR) MODULATORS

(71) Applicant: Charité-Universitätsmedizin Berlin, Berlin (DE)

(72) Inventors: Wolfgang Kübler, Berlin (DE); Lasti Efrinanda Fuaadi, Berlin (DE); Birgitt Gutbier, Berlin (DE); Martin Witzenrath, Berlin (DE)

(73) Assignee: BOREALIS GMBH, Vienna (AT)

( * ) Notice: Subject to any disclaimer, the term of this patent is extended or adjusted under 35 U.S.C. 154(b) by 650 days.

(21) Appl. No.: 18/025,979

(22) PCT Filed: Sep. 17, 2021

(86) PCT No.: PCT/EP2021/075627
§ 371 (c)(1),
(2) Date: Mar. 13, 2023

(87) PCT Pub. No.: WO2022/058503
PCT Pub. Date: Mar. 24, 2022

(65) Prior Publication Data

US 2023/0355607 A1 Nov. 9, 2023

(30) Foreign Application Priority Data

Sep. 18, 2020 (EP) .................................... 20196830

(51) Int. Cl.
*A61K 31/47* (2006.01)
*A61K 31/443* (2006.01)
(Continued)

(52) U.S. Cl.
CPC ............ *A61K 31/47* (2013.01); *A61K 31/443* (2013.01); *A61P 7/10* (2018.01); *A61P 9/14* (2018.01); *A61P 11/00* (2018.01); *A61P 37/02* (2018.01)

(58) Field of Classification Search
CPC .... A61K 31/47; A61K 31/443; A61K 31/404; A61P 7/10; A61P 9/14; A61P 11/00; A61P 37/02; A61P 1/00; A61P 43/00
(Continued)

(56) References Cited

U.S. PATENT DOCUMENTS

2013/0281487 A1* 10/2013 Luisi .................... C07D 215/56 546/156
2014/0073667 A1* 3/2014 Morgan ............... C07D 215/56 546/156

FOREIGN PATENT DOCUMENTS

WO WO 2019099946 A1 * 5/2019

OTHER PUBLICATIONS

Simmons et al, Novel mechanisms regulating endothelial barrier function in the pulmonary microcirculation, J Physiol 597.4 (2019) pp. 997-1021 (Year: 2019).*

(Continued)

*Primary Examiner* — Taylor V Oh
(74) *Attorney, Agent, or Firm* — Lippes Mathias LLP

(57) ABSTRACT

The invention relates to a cystic fibrosis transmembrane conductance regulator (CFTR) modulator for use in the prevention and/or treatment of diseases involving endothelial and/or epithelial barrier dysfunctions. The disease does not comprise cystic fibrosis.
The invention further relates to a pharmaceutical composition comprising a CFTR modulator as an active ingredient for use in the prevention and/or treatment of diseases involving endothelial and/or epithelial barrier dysfunctions.
(Continued)

The invention further relates to a kit of parts for use in the prevention and/or treatment of diseases involving endothelial and/or epithelial barrier dysfunctions comprising i) a CFTR modulator and ii) a further CFTR modulator.
The invention further relates to a method of treating a condition, disease or disorder involving endothelial and/or epithelial barrier dysfunctions in a subject, the method comprising administering a CFTR modulator to a subject, preferably a mammal, in the need thereof.

15 Claims, 19 Drawing Sheets

(51) Int. Cl.
*A61P 7/10* (2006.01)
*A61P 9/14* (2006.01)
*A61P 11/00* (2006.01)
*A61P 37/02* (2006.01)
(58) Field of Classification Search
USPC .......................................................... 514/312
See application file for complete search history.

(56) References Cited

OTHER PUBLICATIONS

"Comparative analysis of antiviral efficacy of FDA-approve drugs against SARS-CoV-2 in human lung cells" dated Aug. 7, 2020 (8pgs).
"Antibacterial Properties of the CFTR Potentiator Ivacaftor" dated Aug. 17, 2020 (11pgs).
"An integrated drug repurposing strategy for the rapid identification of potential SARS-CoV-2 viral inhibitors" dated Aug. 17, 2020 (9pgs).
Ong, Thida, et al. "New Therapeutic Approaches To Modulate and Correct CFTR" Pediatr Clin North Am. Aug. 2016 doi:10.1016/j.pcl.2016.04.006.
Erfinanda, Lasti, et al. "CFTR potentiator attenuates COVID-19 associated lung endothelial barrier failure" European Respiratory Journal, Oct. 29, 2025.

* cited by examiner

Experimental protocol for *in vivo* experiments

Experimental groups:

- Mice non-infected and treated with solvent
- Mice non-infected and treated with Ivacaftor
- Mice infected with *S. pneumoniae* and treated with solvent
- Mice infected with *S. pneumoniae* and treated with Ivacaftor Experimental protocol for *in vivo* experiments – post treatment Experimental groups:

- Mice non-infected and post-treated with solvent
- Mice non-infected and post-treated with Ivacaftor
- Mice infected with *S. pneumoniae* and post-treated with solvent
- Mice infected with *S. pneumoniae* and post-treated with Ivacaftor

MEDICAL USE OF CYSTIC FIBROSIS TRANSMEMBRANE CONDUCTANCE REGULATOR (CFTR) MODULATORS

CROSS REFERENCE TO RELATED APPLICATIONS

This is a 371 of PCT Application No. PCT/EP2021/075627, filed Sep. 17, 2021, which claims the benefit of European Application No. 20196830.2, filed Sep. 18, 2020, the contents of which are incorporated herein in their entirety.

The invention relates to compounds for use in the prevention and/or treatment of diseases involving endothelial and/or epithelial barrier dysfunctions.

The invention further relates to pharmaceutical compositions and to kit of parts for use in the prevention and/or treatment of diseases involving endothelial and/or epithelial barrier dysfunctions.

The invention further relates to methods of preventing and/or treating a condition, disease or disorder involving endothelial and/or epithelial barrier dysfunctions in a subject.

Epithelium lines the outer and inner surfaces of the body, including the inner layer of many internal organs such as the lung, gut, or kidney. As a semi-selective barrier, the epithelium serves both as a protective barrier and as surface for the exchange of selected substances between adjoining compartments. Endothelium lines the interior surface of blood vessels and lymphatic vessels and acts as a semi-selective barrier between the vessel lumen and surrounding tissue, controlling the passage of materials and the transit of white blood cells into and out of the bloodstream. The barrier function of the microvascular endothelium is based on the integrity of the endothelial cell layer and the interendothelial junctions, which undergo moment-to-moment changes in vascular homeostasis, injury and repair at the level of the endothelial cytoskeleton, cell-cell junction complexes, and cell attachments to extracellular matrix and basement membrane.

Epithelial or endothelial barrier dysfunction is a fundamental pathophysiological event that occurs in a variety of diseases. For example, epithelial and/or endothelial barrier dysfunction occurs during stimulation by inflammatory agents, pathogens, or activated immune cells and results in uncontrolled exchange of fluids, small solutes, larger proteins, or even entire cells across compartments.

The acute respiratory distress syndrome (ARDS), in preclinical models also known as acute lung injury (ALI), a common cause of respiratory failure in critically ill patients, is characterized by hyperinflammation and loss of epithelial and endothelial barrier function. It is defined by the acute onset of non-cardiogenic pulmonary edema, hypoxemia, and the need for mechanical ventilation. ARDS is a clinical syndrome triggered by various pathologies such as trauma, pneumonia, and/or sepsis (Matthay et. al, Nat Rev Dis Primers. 2019 Mar. 14; 5(1):18).

ARDS was initially defined in 1967 with a case-based report that described the clinical presentation in critically ill adults and children of acute hypoxemia, non-cardiogenic pulmonary edema, reduced lung compliance (increased lung stiffness), increased work of breathing, and the need for positive pressure ventilation in association with several clinical disorders including trauma, pneumonia, sepsis and aspiration of gastric contents. In 1992, an American-European consensus conference established specific diagnostic criteria for the syndrome; these criteria were updated in 2012 in the so-called Berlin Definition of ARDS in adults.

ARDS develops most commonly in the setting of pneumonia (bacterial and viral including SARS-COV-2; fungal is less common), non-pulmonary sepsis (with sources that include the peritoneum, urinary tract, soft tissue and skin), VILI (ventilator induced lung injury) and SIRS (systemic inflammatory response syndrome), aspiration of gastric and/or oral and esophageal contents (which may be complicated by subsequent infection) and major trauma (such as blunt or penetrating injuries or burns). Several other less common scenarios are also associated with the development of ARDS, including acute pancreatitis; transfusion of fresh frozen plasma, red blood cells and/or platelets (that is, transfusion-associated acute lung injury (TRALI)); drug overdose with various agents; near drowning (inhalation of fresh or salt water); haemorrhagic shock or reperfusion injury (including after cardiopulmonary bypass and lung resection); and smoke inhalation (often associated with cutaneous burn injuries). Other causes of non-cardiogenic pulmonary edema that are often considered as additional etiologies of ARDS include primary graft dysfunction following lung transplantation, high altitude pulmonary edema, neurogenic pulmonary edema, and drug-induced lung injury.

Sepsis is a life-threatening condition that arises when the body's response to infection causes injury to its own tissues and organs. Sepsis is caused by an inflammatory immune response triggered by an infection. Most commonly, the infection is bacterial, but it may also be fungal, viral, or protozoan. Common locations for the primary infection include the lungs, brain, urinary tract, skin, and abdominal organs. The most common cause of sepsis is pneumonia. Endothelial barrier dysfunction is a fundamental pathophysiological event that occurs also early in sepsis and septic shock in particular. Under physiological conditions, the integrity of the endothelium is maintained by the cell cytoskeleton (actin), intercellular adhesion molecules (tight junctions), adherens junctions and an array of supportive proteins, in order to maintain intercellular adhesion. In sepsis and upon other pro-inflammatory stimuli, endothelial activation occurs and these structures are disrupted primarily in response to platelet and neutrophil adhesion, the release of inflammatory mediators and toxic oxidative and nitrosative intermediates. Combined with the increased expression of selectins and integrins, binding of leukocytes to the endothelial surface results in the paracellular leakage of vascular fluid and migration of extravasating leukocytes across the compromised endothelial barrier (Hotchkiss et al., Nat Rev Dis Primers. 2016 Jun. 30; 2:16045).

Systemic inflammatory response syndrome (SIRS) is an inflammatory state affecting the whole body. It is the body's response to an infectious or noninfectious insult. SIRS is a serious condition related to systemic inflammation, organ dysfunction, and organ failure. SIRS is also closely related to sepsis, in which patients satisfy criteria for SIRS and have a suspected or proven infection.

Pneumonia is an inflammatory condition of the lung affecting primarily the small air sacs known as alveoli. Typically symptoms include combinations of productive or dry cough, chest pain, fever, and troubled breathing. Pneumonia is usually caused by infection with viruses or bacteria and less commonly by other microorganisms, certain medications and conditions such as autoimmune diseases.

In ARDS, there is increased permeability to liquid and protein across the lung endothelium which then leads to accumulation of edema in the lung interstitium. Next, the edema fluid translocates into the alveoli, often facilitated by injury to the normally tight barrier properties of the alveolar epithelium. Increased alveolar-capillary permeability to fluid, protein, neutrophils and erythrocytes (resulting in their accumulation into the alveolar space) is the hallmark of ARDS.

Once lung injury occurs, protein-rich inflammatory edema fluid accumulates in the lung interstitium and the distal air spaces, as described above. Interstitial and alveolar edema are key features of diffuse alveolar damage (DAD) in the acute "exudative" phase (~7 days) of ARDS. Pathologic specimens from patients with ARDS most frequently reveal diffuse alveolar damage (DAD), and laboratory studies have demonstrated both alveolar epithelial and lung endothelial injury, resulting in accumulation of protein-rich inflammatory edema fluid in the alveolar space.

ARDS is usually treated by respiratory support (including oxygen supplementation and positive pressure ventilation), careful fluid management, appropriate antimicrobial therapy, and general supportive measures such as nutritional supplementation. However, mechanistic treatment strategies targeting hyperinflammation or barrier failure as key pathologic features of the disease are yet lacking. Moreover, an adverse consequence of mechanical ventilation called ventilator-induced lung injury (VILI) can result in pulmonary edema, barotrauma, and worsening hypoxemia that can prolong mechanical ventilation, lead to multi-system organ dysfunction, and increase mortality. Attempts have been made for preventative therapies implemented early in the progression of acute lung injury, before patients meet ARDS diagnostic criteria, which could improve clinical outcomes. Until now, all trials focused on prevention using pharmacotherapies have met with disappointing results.

There is thus a need and accordingly it is the object of the present invention to provide new therapies for the prevention and/or treatment of diseases involving endothelial and/or epithelial barrier dysfunctions, in particular acute respiratory distress syndrome (ARDS), ventilator induced lung injury (VILI), systemic inflammatory response syndrome (SIRS), transfusion-associated acute lung injury (TRALI), sepsis or pneumonia.

The present invention is based on the surprising finding that in order to prevent and/or alleviate diseases involving endothelial and/or epithelial barrier dysfunctions, the cystic fibrosis transmembrane conductance regulator (CFTR) protein is a target for such new therapies. Specifically, it is based on the surprising finding that a CFTR modulator can be successfully applied in the natural occurring non-mutant CFTR genetic background.

The present invention therefore provides a cystic fibrosis transmembrane conductance regulator (CFTR) modulator or a pharmaceutical composition comprising, preferably consisting of a CFTR modulator as an active ingredient for use in the prevention and/or treatment of diseases involving endothelial and/or epithelial barrier dysfunctions, in particular acute respiratory distress syndrome (ARDS), ventilator induced lung injury (VILI), systemic inflammatory response syndrome (SIRS), transfusion-associated acute lung injury (TRALI), sepsis, or pneumonia including COVID-associated pneumonia.

The invention further provides a kit of parts for use in the prevention and/or treatment of diseases involving endothelial and/or epithelial barrier dysfunctions comprising, preferably consisting of i) a CFTR modulator and ii) a further CFTR modulator.

The invention further provides methods of preventing and/or treating a condition, disease or disorder involving endothelial and/or epithelial barrier dysfunctions in a subject the method comprising administering a CFTR modulator to a subject, in the need thereof.

Preferably, the subject is a mammal, more preferably a human mammal.

Endothelial and/or epithelial barrier dysfunction is defined as an increase in paracellular permeability of the endothelial and/or epithelial barrier.

Endothelial and/or epithelial barrier dysfunction is the result of disruption of the intercellular integrity of the endothelium or epithelium. Hence, the endothelial and/or epithelial barrier integrity is thus not maintained. This functional integrity (intercellular adhesion) is reduced primarily by intercellular gap formation. Thereby the epithelial and endothelial barriers become more permeable. Hence, endothelial and/or epithelial barrier dysfunction is characterized by increased paracellular permeability.

The pathophysiology of epithelial and endothelial barrier dysfunction is characterized by increased flux of liquid and solutes of different size (according to the size of the intercellular gaps) across the barrier. Hence, epithelial or endothelial barrier dysfunction can be measured by several methods known in the art useful for determining the paracellular permeability of the epithelial or endothelial barrier.

For example, epithelial barrier dysfunction can be measured by determining the transcellular resistance, by measuring an increase in epithelial calcium, by measuring fluid flux across the epithelial barrier, or by measuring the translocation of macromolecules or cells such as serum albumin, leukocytes, polymorphonuclear neutrophils, inflammatory macrophages, for example between compartments separated by an epithelial layer.

For example, endothelial barrier dysfunction can be measured by determining the transcellular resistance, by measuring an increase in endothelial calcium, by measuring fluid flux across the endothelial barrier, or by measuring the translocation of macromolecules or cells such as serum albumin, leukocytes, polymorphonuclear neutrophils, inflammatory macrophages from the blood into the interstitium or adjoining compartments such as alveoli (in the lung).

For example, endothelial and epithelial barrier dysfunction can be measured by determining the accumulation of total protein, serum albumin, immunoglobulins, or leukocytes in the interstitium or in the surrounding tissue. Similarly, endothelial or epithelial barrier dysfunction can be determined by measuring the translocation of intravenously infused exogeneous tracers (radioactively labeled, dyes such as Evans Blue, etc) into the interstitium or surrounding tissue (in case of the lung these markers can be retrieved from the bronchoalveolar lavage fluid (BALF)), or—in case of the lung—the uptake of endogenous (surfactant proteins, RAGE (receptor for advanced glycation endproducts)) or exogenous (radioactively labeled, dyes, other macromolecules) from the lung airspaces into the blood stream. In cell culture, endothelial or epithelial barrier dysfunction can be determined by measuring of trans-epithelial or—endothelial electrical resistance or impedance, by microscopic visualization of intercellular gaps, loss of junctional proteins, increased calcium signals, or the formation of actin stress fibers.

Exemplary diseases involving an endothelial barrier and/or epithelial dysfunction are ARDS, VILI, SIRS, TRALI, sepsis, pneumonia incl. COVID-19 associated pneumonia, metastatic cancer cell intra- and extravasation, vascular diseases such as atherosclerosis or coronary artery disease, diabetes mellitus, hypertension, hypercholesterolemia, rheumatoid arthritis, systemic lupus erythematosus, Ischemia-reperfusion injury, local or systemic infections such as e.g. Dengue fever, local or systemic allergic reactions including anaphylactic shock.

The disease involving endothelial and/or epithelial barrier dysfunction does not comprise cystic fibrosis. In particular, cystic fibrosis does not involve an endothelial and/or epithelial barrier dysfunction as defined herein which is characterized by increased paracellular permeability. Cystic fibrosis is a genetic disorder involving mutations of the CFTR gene coding for the ABC transporter-class ion channel protein CFTR that conducts chloride ions across epithelial cell membranes. Depending on the type of mutation, the channel is defective and/or present only in minor amounts impairing the chloride transport. Hence, cystic fibrosis is characterised by impaired transcellular permeability for $Cl^-$ ions. In contrast, diseases involving endothelial and/or epithelial barrier dysfunction typically occur in patients with no mutations in CFTR and are thus non-genetic diseases, which have thus a different cause such as infectious pathogens.

Preferably, the disease involving endothelial and/or epithelial barrier dysfunction does not comprise diseases involving a mutation of the CFTR gene. The disease involving endothelial and/or epithelial barrier dysfunction comprises diseases wherein the CFTR gene is not mutated.

Moreover, the disease involving endothelial and/or epithelial barrier dysfunction does not comprise diseases involving a hydrostatic pulmonary edema. Hydrostatic edema refers to accumulation of excess interstitial fluid which results from elevated capillary hydrostatic pressure. Hydrostatic pulmonary edema involves an abnormal increase in extravascular water secondary to elevated pressure in the pulmonary circulation, as in congestive heart failure or intravascular volume overload. Hydrostatic pulmonary edema does not involve an endothelial barrier dysfunction as defined herein.

Epithelial and/or endothelial dysfunction may lead to edema. Preferably, the CFTR modulator is used for the prevention and/or treatment of diseases involving a permeability-type edema. Permeability-type edema results from disruption of the endothelial and/or the epithelial cell layer in the microvascular wall so that the barrier is less able to restrict the movement of macromolecules from the blood to interstitium.

The permeability-type edema may be a pulmonary edema. Preferably, the CFTR modulator is used for the prevention and/or treatment of diseases involving a pulmonary permeability-type edema.

Pulmonary edema is defined as fluid accumulation in the tissue and air spaces of the lungs. It leads to impaired gas exchange and may cause respiratory failure. The causes of pulmonary edema can be divided into cardiogenic (hydrostatic) and non-cardiogenic (permeability-type). For cardiogenic pulmonary edema it is due to failure of the left ventricle of the heart to remove blood adequately from the pulmonary circulation. For non-cardiogenic pulmonary edema it is due to an injury to the lung parenchyma or vasculature of the lung. A non-cardiogenic pulmonary edema is rich in proteins and inflammatory cells whereas the cardiogenic pulmonary edema involves only few protein and inflammatory cells. The pulmonary permeability-type edema is non-cardiogenic. In contrast, the cardiogenic lung edema is the most common form of hydrostatic pulmonary edema as defined above.

The disease involving an endothelial barrier and/or epithelial dysfunction may be acute or chronic. Acute illnesses generally develop suddenly and last a short time, often only a few days or weeks. Chronic conditions develop slowly and may worsen over an extended period of time. Preferably, CFTR modulator is used for the prevention and/or treatment of acute diseases.

Preferably, the CFTR modulator is used for the prevention and/or treatment of inflammatory diseases. The inflammation may be caused by a non-infectious stimulus or insult or by an infectious agent.

Preferably, the non-infectious stimulus or insult is an inhalative irritant, mechanical ventilation, trauma, burn, pancreatitis, uremia, transfusion related, disseminated coagulopathy, ischemia-reperfusion, transplantation, acid aspiration, idiopathic (Haman-Rich Syndrome) and any other sterile cause of ARDS, VILI, SIRS, TRALI or pneumonia.

Preferably, the infectious agent is bacterial, viral, or fungal. Fungi include *Histoplasma capsulatum, blastomyces, Cryptococcus neoformans, Pneumocystis jiroveci, pneumocystis* pneumonia, *Coccidioides immitis*. Bacteria include *Haemophilus* influenza, *Staphylococcus aureus, Pseudomonas* species such as *Pseudomonas aeruginosa, Klebsiella pneumoniae, Mycoplasma pneumoniae, Chlamydophila pneumoniae, Legionella pneumophila, Moraxella catarrhalis, Streptococcus* species such as *Streptococcus pneumoniae, Streptococcus viridans, Streptococcus faecalis, Enterobacter, Salmonella, Escherichia coli, Proteus, Serratia, Neisseria meningitidis*. Viruses include rhinoviruses, coronaviruses, such as SARS-COV-1 or SARS-COV-2, influenza virus, respiratory syncytial virus (RSV), adenovirus, parainfluenza, herpes simplex virus, or cytomegalovirus pneumonia. More preferably, the infectious agent is bacterial or viral selected from *Streptococcus pneumoniae, Haemophilus influenzae, Chlamydophila pneumoniae*, rhinoviruses, coronaviruses, influenza virus, respiratory syncytial virus, adenovirus, or parainfluenza. Most preferably, the infectious agent is *Streptococcus pneumoniae* or SARS-COV-2.

Preferably, the CFTR modulator is used for the prevention and/or treatment of an infectious disease. The infectious disease is caused by an infectious agent as defined above.

Preferably, the CFTR modulator is used for the prevention and/or treatment of a pulmonary disease, a renal disease, an intestinal disease, SIRS or sepsis.

Preferred renal diseases include acute kidney injury, hemolytic-uremic syndrome, or chronic kidney disease.

Preferred intestinal diseases include inflammatory bowel disease (IBD).

Preferred pulmonary diseases include ARDS, VILI, TRALI or pneumonia. Exemplary types of pneumonia include community-acquired pneumonia (CAP) and hospital-acquired pneumonia (HAP). CAP further includes sCAP (severe community-acquired pneumonia). sCAP is present when the inflammation localized in the lungs spreads generalized to the body and leads to sepsis-associated complications such as sepsis, septic shock or organ failure. Ventilator-associated pneumonia (VAP) is a special form of HAP.

For CAP common pathogens are *Streptococcus pneumoniae*, influenza virus, *Haemophilus influenzae, Mycoplasma pneumoniae, Chlamydophila pneumoniae* and rarely *Legionella pneumophila*. For HAP common pathogens are *Pseudomonas aeruginosa, Enterobacter, E. coli, Proteus, Serratia, Klebsiella pneumoniae* and further multiresistant pathogens.

Preferably, the CFTR modulator is used for the prevention and/or treatment of pulmonary diseases, SIRS, COVID-19, or sepsis. Preferred pulmonary disease are defined above.

Preferably, the CFTR modulator is used for the prevention and/or treatment of ARDS, VILI, SIRS, TRALI, sepsis, or pneumonia including COVID-19 associated pneumonia. More preferably, the CFTR modulator is used for the prevention and/or treatment of ARDS, sepsis, or pneumonia including COVID-19 associated pneumonia. Most preferred the CFTR modulator is used for the prevention and/or treatment of ARDS, or pneumonia including COVID-19 associated pneumonia.

Preferably, the CFTR modulator is used for the prevention and/or treatment of the symptoms of ARDS, VILI, SIRS, TRALI, sepsis, or pneumonia including COVID-19 associated pneumonia, including an accumulation of interstitial or alveolar fluid in the lung, hypoxemia, cough, wheezing, dyspnea, hyperpnea and pulmonary inflammation, more preferably of the symptoms of ARDS, sepsis, or pneumonia including COVID-19 associated pneumonia, most preferred of the symptoms of ARDS or pneumonia including COVID-19 associated pneumonia. On a cellular level, these symptoms are evident as increased neutrophil and macrophage accumulation in the bronchoalveolar lavage fluid.

The cystic fibrosis transmembrane conductance regulator (CFTR) protein is a member of the ABC transporter family. CFTR is expressed in a variety of cell types, including absorptive and secretory epithelia cells, where it regulates the anion flux across the membrane, as well as the activity of other ion channels and proteins. More specifically, it is a chloride channel present at the surface of epithelial cells in multiple organs. Moreover, CFTR is expressed in numerous tissues and cell types, including lung endothelial cells. CFTR is downregulated from the cell surface in infectious and inflammatory conditions. Moreover, inhibition of CFTR was found to increase lung microvascular endothelial permeability in vitro.

A CFTR modulator is defined as a compound that improves CFTR function—commonly defined as chloride flux through the channel—in cells, organs or organisms with defective CFTR protein due to a mutation of the CFTR gene.

The primary function of the CFTR protein is to create a channel for chloride to flow across the cell surface. A defective CFTR protein is defined herein as caused by mutations in the CFTR gene.

The chloride flow can be measured by methods known in the art for example by measuring single channel activity by patch clamp technique, by measurement of short circuit currents in Ussing chambers, or by measuring changes in intracellular $Cl^-$ by $Cl^-$ sensitive fluorescent dyes as a function of extracellular $Cl^-$ concentrations.

CFTR modulators have been developed for use in the treatments of cystic fibrosis wherein in the cystic fibrosis transmembrane conductance regulator (CFTR) gene that affect the production of the CFTR protein is mutated. Specifically, CFTR modulators have been designed to correct defects of the CFTR protein caused by such mutations in the CFTR gene. In essence, a defective CFTR protein results in a decreased chloride flux across the cell membrane. CFTR modulators have been shown to effectively target specific defects in the CFTR protein. As a group, these drugs are called modulators because they are intended to modulate, i.e. improve the function of the defective CFTR protein so that it can serve its primary function.

The instant invention uses CFTR modulators in diseases which do not involve a mutation of the CFTR gene and thus do not suffer from defective CFTR protein.

The modulators fall into three categories, that is CFTR potentiators, CFTR correctors and CFTR amplifiers.

A CFTR potentiator is defined as a compound that increases the channel open probability (or gating) of the defective CFTR protein. That can be determined again by determining the chloride flux.

The CFTR protein is shaped like a tunnel that can be closed by a gate. CFTR potentiators were designed to increase the open probability of CFTR channels that are available at the membrane but have gating (Class III) and conductance (Class IV) mutations.

Preferably, the CFTR potentiator is a compound selected from Ivacaftor (CAS No.: 873054-44-5, commercially available under the tradename Kalydeco® by Vertex Pharmaceuticals), GLPG2451 (CAS No.: 2055015-61-5 commercially available from Galapagos NV) and GLPG1837 (CAS No.: 1654725-02-6 commercially available from Galapagos NV), QBW251 (commercially available from Novartis), PTI-808 (commercially available from Proteostasis Therapeutics), FDL176 (commercially available from Flatley Discovery Lab) or derivatives or pharmaceutically acceptable salts thereof.

Ivacaftor (CAS No.: 873054-44-5, Vertex Pharmaceuticals) is N-(5-hydroxy-2,4-ditert-butyl-phenyl)-4-oxo-1H-quinoline-3-carboxamide and has the following structural Formula I:

Formula I

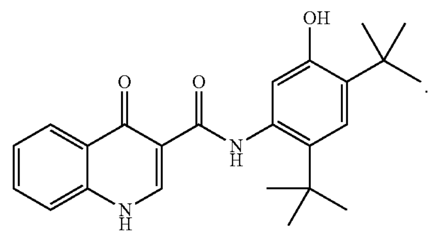

GLPG2451 (CAS No.: 2055015-61-5, Galapagos NV) is a compound having the following structural Formula II:

Formula II

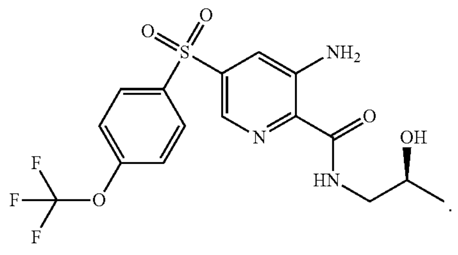

GLPG1837 (CAS No.: 1654725-02-6, Galapagos NV) is N-(3-carbamoyl-5,5,7,7-tetramethyl-4,7-dihydro-5H-thieno[2,3-c]pyran-2-yl)-1H-pyrazole-3-carboxamide and has the following structural Formula III:

Formula III

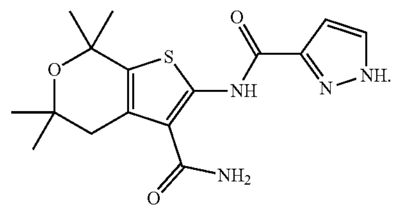

A CFTR corrector is defined as a compound which improves correct folding of the nascent amino acid chain translated from a mutated CFTR gene into its correct three dimensional structure and/or improves trafficking of the protein product of the mutated CFTR gene to the cell membrane, and/or increases the stability of the protein product of the mutated CFTR gene at the cell membrane.

This leads to more functional protein at the cell membrane which can again be determined by measuring the chloride flux across the cell membrane.

CFTR correctors have been designed for cystic fibrosis patients which have at least one copy of the F508del mutation, which prevents the CFTR protein from forming the right three dimensional shape (Class II mutation). A CFTR corrector helps the CFTR protein to form the right three dimensional shape so that it is able to move to the cell surface. Thus, a CFTR corrector can increase the amount of functional CFTR protein at the cell membrane.

Preferably, the CFTR corrector is a compound selected from Lumacaftor (CAS No.: 936727 May 8, VX 809, commercially available from Vertex Pharmaceuticals), Tezacaftor (CAS No.: 1152311-62-0, VX 661, commercially available from Vertex Pharmaceuticals), Elexacaftor (CAS No.: 2216712-66-0, VX 445, commercially available from Vertex Pharmaceuticals), Bamocaftor (CAS No.: 2204245-48-5, VX 659 commercially available from Vertex Pharmaceuticals), Bamocaftor potassium (CAS 2204245-47-4, VX 659 potassium salt commercially available from Vertex Pharmaceuticals) Posenacaftor (CAS No.: 2095064 May 2, PTI-801, commercially available from Proteostasis Therapeutics), Cavosonstat (CAS No.: 1371587-51-7, N91115, commercially available from Nivalis Therapeutics), GLPG2222 (CAS No.: 1918143-53-9, commercially available from Galapagos NV), GLPG2737 (commercially available from Galapagos NV), or derivatives, or pharmaceutically acceptable salts thereof.

Lumacaftor (CAS No.: 936727 May 8, VX 809, Vertex Pharmaceuticals) is 3-[6-({[1-(2,2-difluoro-1,3-benzodioxol-5-yl)cyclopropyl]carbonyl}amino)-3-methylpyridin-2-yl]benzoic acid and has the following structural Formula IV:

Formula IV

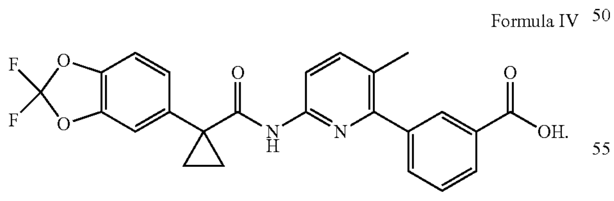

Tezacaftor (CAS No.: 1152311-62-0 Vertex Pharmaceuticals) is 1-(2,2-difluoro-1,3-benzodioxol-5-yl)-N-[1-[(2R)-2,3-dihydroxypropyl]-6-fluoro-2-(1-hydroxy-2-methylpropan-2-yl) indol-5-yl]cyclopropane-1-carboxamide and has the following structural Formula V:

V

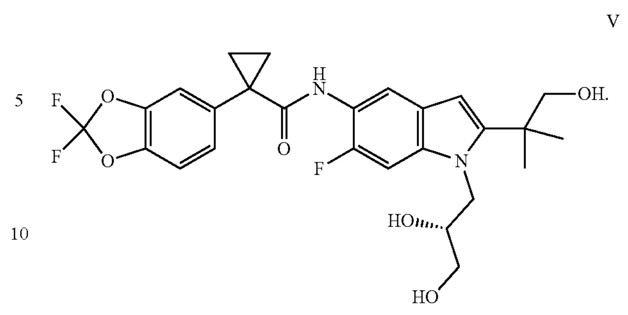

Elexacaftor (CAS No.: 2216712-66-0 Vertex Pharmaceuticals) is N-(1,3-dimethylpyrazol-4-yl) sulfonyl-6-[3-(3,3,3-trifluoro-2,2-dimethylpropoxy) pyrazol-1-yl]-2-[(4S)-2,2,4-trimethylpyrrolidin-1-yl]pyridine-3-carboxamide and has the following structural Formula VI:

Formula VI

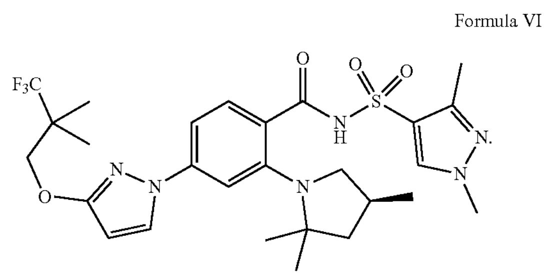 [SMILES: Cc1nn(C)cc1S(=O)(=O)NC(=O)c1ccc(-n2ccc(OCC(C)(C)C(F)(F)F)n2)cc1N1C[C@@H](C)CC1(C)C]

Bamocaftor (CAS No.: 2204245-48-5, Vertex Pharmaceuticals) is (S)—N-(phenylsulfonyl)-6-(3-(2-(1-(trifluoromethyl)cyclopropyl) ethoxy)-1H-pyrazol-1-yl)-2-(2,2,4-trimethylpyrrolidin-1-yl) nicotinamide and has the following structural Formula VII:

Formula VII

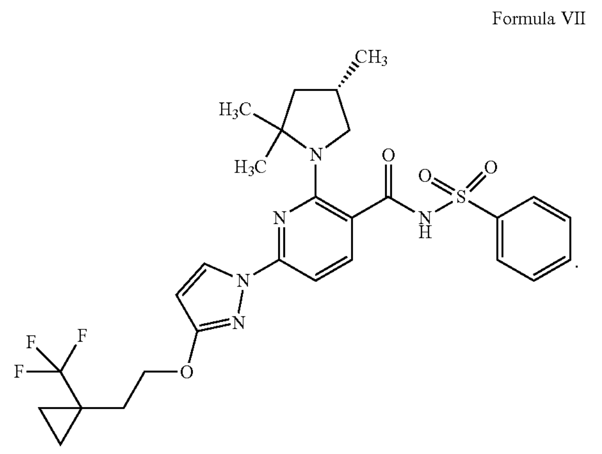 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

Bamocaftor potassium (CAS 2204245-47-4, Vertex pharamceuticals) is Potassium (benzenesulfonyl) [6-(3-[2-[1-(trifluoromethyl)cyclopropyl]ethoxy]-1H-pyrazol-1-yl)-2-[(4S)-2,2,4-trimethylpyrrolidin-1-yl]pyridine-3-carbonyl] azanide and has the structural Formula VII.

Posenacaftor (CAS No.: 2095064 May 2, PTI-801 Proteostasis Therapeutics) is 8-methyl-2-(3-methyl-1-benzofuran-2-yl)-5-[(1R)-1-(oxan-4-yl) ethoxy]quinoline-4-carboxylic acid and has the following structural Formula VIII:

Formula VIII

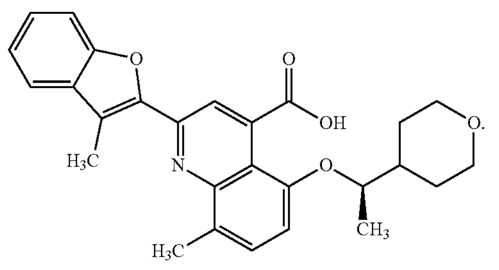

Cavosonstat (CAS No.: 1371587-51-7, N91115, *Nivalis* Therapeutics) is 3-Chloro-4-(6-hydroxy-2-quinolinyl)benzoic acid and has the following structural Formula IX:

Formula IX

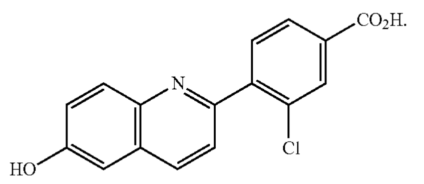

GLPG2222 (CAS No.: 1918143-53-9, Galapagos NV) is 4-[(2R,4R)-4-[[1-(2,2-difluoro-1,3-benzodioxol-5-yl)cyclopropanecarbonyl]amino]-7-(difluoromethoxy)-3,4-dihydro-2H-chromen-2-yl]benzoic acid and has the following structural Formula X:

Formula X

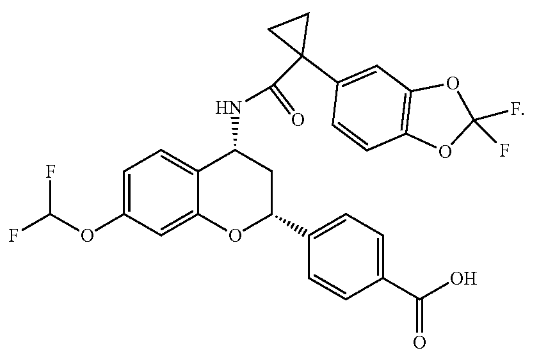

A CFTR amplifier is defined as a compound which increases the amount of mutant CFTR messenger RNA, and consequently the amount of CFTR protein.

The amount of messenger RNA can be determined by methods known in the art such as Northern blot or RT-PCR.

CFTR amplifiers are designed for CFTR mutations which produce insufficient CFTR protein. CFTR amplifiers are a class of drugs that increase CFTR protein levels in cells and tissues. As CFTR amplifiers increase the amount of mutant CFTR messenger RNA, and consequently the amount of CFTR protein, they thereby increase the substrates for other CFTR modulators. Messenger RNA is an intermediate molecule containing a copy of the genetic code specifying the amino acid sequence of a protein. Amplifiers by themselves do not correct or improve the function of the CFTR protein.

Preferably, the CFTR amplifier is a compound selected from Nesolicaftor (PTI-428, commercially available from Proteostasis Therapeutics) and PTI-CH (Kenneth A. Giuliano et. al., SLAS Discov. 2018 February; 23(2): 111-121) or derivatives, or pharmaceutically acceptable salts thereof.

Nesolicaftor (PTI-428, Proteostasis Therapeutics) is a compound having the following structural Formula XI:

Formula XI

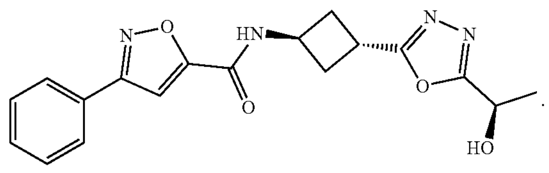

Preferably, the CFTR modulator is a CFTR potentiator, CFTR corrector or a CFTR amplifier. More preferably, the CFTR modulator is a CFTR potentiator or a CFTR corrector.

Preferably, the CFTR potentiator is a compound having the structural formula I, or derivatives, or pharmaceutically acceptable salts thereof.

Preferably, the CFTR corrector is a compound having the structural formula IV to VII, or derivatives, or pharmaceutically acceptable salts thereof. More preferably, the CFTR corrector is a compound having the structural formula IV or derivatives, or a pharmaceutically acceptable salt thereof.

Preferably, the CFTR modulator is a compound having the structural formula I or IV, or derivatives or pharmaceutically acceptable salts thereof.

If derivatives are used, then preferably the CFTR modulator derivative is a deuterated derivative. The replacement of hydrogen with deuterium in drug molecules can lead to significant alterations in their metabolism and thereby cause beneficial changes in the biological effects of drugs, such as their pharmacokinetics by decreasing their rate of metabolism allowing less frequent dosing. The deuterated derivative is preferably a compound according to structural Formula I or IV wherein one or more hydrogens are replaced by deuterium.

Deutivacaftor (CAS No.: 1413431-07-8, deuterated Ivacaftor or VX 561 commercially available from Vertex Pharmaceuticals) is N-[2-tert-butyl-4-[1,1,1,3,3,3-hexadeuterio-2-(trideuteriomethyl) propan-2-yl]-5-hydroxy-phenyl]-4-oxo-1H-quinoline-3-carboxamide and has the following structural Formula XIII:

Formula XIII

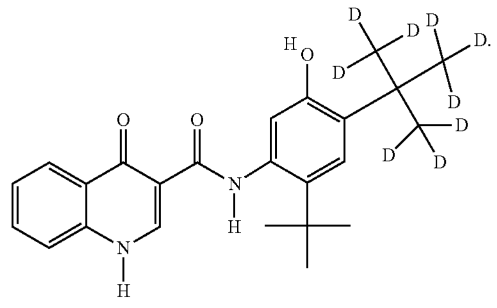

More preferably, the CFTR modulator is a compound having the structural Formula I or IV, or a pharmaceutically acceptable salt thereof.

Even more preferably, the CFTR modulator is Ivacaftor or Lumacaftor.

In the present invention it is to be understood that any preferred embodiment disclosed for the disease involving endothelial and/or epithelial barrier dysfunctions may be combined with any preferred embodiment for the CFTR modulator. Preferably, the invention relates to a CFTR modulator having the structural formula I or IV, or derivatives or pharmaceutically acceptable salts thereof for use in the prevention and/or treatment of ARDS, VILI, SIRS, TRALI, sepsis or pneumonia.

More preferably, the invention relates to a CFTR modulator having the structural formula I or IV, or pharmaceutically acceptable salts thereof for use in the prevention and/or treatment of ARDS, VILI, SIRS, TRALI, sepsis or pneumonia.

Most preferably, the CFTR modulator as used in the present invention is Ivacaftor or Lumacaftor (CAS No.: 873054-44-5 or CAS No.: 936727-05-8 both commercially available from Vertex Pharmaceuticals) for use in the prevention and/or treatment of ARDS, VILI, SIRS, TRALI, sepsis or pneumonia.

The CFTR modulator as used in the present invention may be administered by any suitable route of administration. Preferably, the CFTR modulator is administered by systemic administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages.

More preferably, the CFTR modulator is administered by injection or infusion, more preferably intravenous injection or infusion.

The use of the present invention also comprises embodiments in which the CFTR modulator is used in combination with one or more further active ingredient. In the present invention, the CFTR modulator may be used in combination with one or more further CFTR modulators. It is to be understood that the one or more further CFTR modulators are different from the CFTR modulator for use, i.e. a combination of different CFTR modulators may be used. For example, a CFTR potentiator or CFTR corrector may used in combination with a further CFTR modulator. Particularly, a CFTR potentiator may be used in combination with a CFTR corrector. Particularly a CFTR potentiator having the structural formula I, or derivatives or pharmaceutically acceptable salts thereof may be used in combination with a CFTR corrector, specifically having the structural formula IV or V or derivatives or pharmaceutically acceptable salts thereof. Particularly, Ivacaftor may be used in combination with a CFTR corrector selected from Lumacaftor or Tezacaftor.

The CFTR modulators are usually formulated into pharmaceutical compositions. Hence, in a further aspect, the invention relates to a pharmaceutical composition comprising, preferably consisting of a CFTR modulator as an active ingredient for use in the prevention and/or treatment of diseases involving endothelial and/or epithelial barrier dysfunctions. The pharmaceutical compositions may optionally further comprise one or more additional pharmaceutically active compounds including one or more further CFTR modulators as defined above and/or a combination thereof. Further, pharmaceutically acceptable excipient meaning a pharmaceutically acceptable material, composition or vehicle involved in giving form or consistency to the pharmaceutical composition may be present in the pharmaceutical compositions.

In a further aspect, the invention relates to a kit of parts for use in the prevention and/or treatment of diseases involving endothelial and/or epithelial barrier dysfunctions comprising, preferably consisting of i) a CFTR modulator, and ii) a further CFTR modulator as defined above. Particularly, i) may be a CFTR potentiator or a CFTR corrector, and ii) may be a further CFTR modulator. Particularly, i) may be a CFTR potentiator, and ii) may be a CFTR corrector. Particularly, i) may be a CFTR potentiator having the structural formula I, or derivatives or pharmaceutically acceptable salts thereof and ii) may be a CFTR corrector, particularly having the structural formula IV or V or derivatives or pharmaceutically acceptable salts thereof. Particularly, i) may be Ivacaftor and ii) may be a CFTR corrector selected from Lumacaftor or Tezacaftor.

The components for a kit of parts of the invention may be formulated for simultaneous administration or for administration in any sequence. The components may also be for repeated administration.

In a further aspect, the invention relates to a method of preventing and/or treating a condition, disease or disorder involving endothelial and/or epithelial barrier dysfunctions the method comprising administering a CFTR modulator to a subject.

Preferably, the subject is in need of such prevention and/or treatment. Preferably, the subject is a mammal, in the need thereof.

In the present invention, it is to be understood that any embodiment disclosed for the CFTR modulator for use and any embodiment disclosed for the diseases involving endothelial and/or epithelial barrier dysfunctions is applicable for either the pharmaceutical composition comprising, preferably consisting of a CFTR modulator as an active ingredient, the kit of parts comprising, preferably consisting of i) a CFTR modulator, and ii) a further CFTR modulator and the method of preventing and/or treating a condition, disease or disorder involving endothelial and/or epithelial barrier dysfunctions, the method comprising administering a CFTR modulator to a subject.

The invention is now further illustrated by the following figures and examples.

FIG. 1. Group data show that CFTR modulators reduce lung endothelial permeability after stimulation with toxin from *S. pneumoniae*, pneumolysin (PLY), in in vitro experiments.

(A) Reduced resistance of human pulmonary microvascular endothelial cells (HPMECs) after stimulation with PLY. Pre-treatment with Ivacaftor confers a protective effect on HPMECs resistance and permeability.

(B) Reduced resistance of human pulmonary microvascular endothelial cells (HPMECs) after stimulation with PLY. Pre-treatment with Lumacaftor confers a protective effect on HPMECs resistance and permeability.

(C) PLY stimulation reduced CFTR expression on HPMECs and pre-treatment with Ivacaftor rescued the CFTR expression after PLY stimulation.

FIG. 2. Group data show Ivacaftor reduced the increase in intracellular Ca2+ concentration ([Ca2+]i) in response to pneumolysin in in vitro experiment. Stimulation with pneumolysin (PLY), toxin from *S. pneumoniae*, at t=30 min in human pulmonary microvascular endothelial cells (HP-MECs) increased endothelial [Ca2+]i and Ivacaftor pretreatment attenuated this endothelial [Ca2+]i increase. Data are mean±SEM, *p<0.05 vs control, n=6-12 each group.

FIG. 3. Group data show CFTR modulators reduced lung permeability after stimulation with toxin from *S. pneumoniae*, pneumolysin (PLY), in ex vivo experiment. PLY stimulation increased lung permeability and edema formation that is evident as increased lung weight gain in isolated perfused mouse lungs and Ivacaftor pre-treatment was able to reduce this effect.

FIG. 4. Group data show that Ivacaftor reduced lung edema formation in in vivo experiments. Experimental protocol for in vivo experiments (A) *S. pneumoniae* infection increased protein leakage in the mouse lung, as demonstrated by higher (B) mouse serum albumin (endogenous marker) and (C) human serum albumin (HSA) (exogenous marker infused intravenously 60 min prior to euthanasia) in the bronchoalveolar lavage fluid (BALF). Ivacaftor pre-treatment reduced the protein leakage to the lung showing that Ivacaftor has a protective effect on endothelial barrier function in the *S. pneumoniae* infected lung. (D) Ivacaftor pre-treatment increased survival rate in *S. pneumoniae* infected mice. (E) *S. pneumoniae* infection reduced CFTR expression and Ivacaftor pre-treatment stabilized the expression of CFTR in lungs of mice infected with *S. pneumoniae*. Data are mean±SEM, *p<0.05 vs control, n=6-12 each group.

FIG. 5. Group data show Ivacaftor reduced pulmonary immune response in in vivo experiment. *S. pneumoniae* infection increased (A) leukocytes, (B) polymorphonuclear cells (PMN), and (C) inflammatory macrophages in the bronchoalveolar lavage fluid (BALF). Ivacaftor pre-treatment reduced the pulmonary immune response to the lung showing that Ivacaftor has a protective effect in the *S. pneumoniae* infected lung.

FIG. 6. Group data show that Ivacaftor post treatment reduced lung edema formation in in vivo experiments. Experimental protocol for in vivo experiments (A). *S. pneumoniae* infection increased protein leakage in the mouse lung, as demonstrated by higher (B) mouse serum albumin (endogenous marker) and (C) human serum albumin (HSA) (exogenous marker infused intravenously 60 min prior to euthanasia) in the bronchoalveolar lavage fluid (BALF). Ivacaftor post-treatment reduced the protein leakage to the lung showing that Ivacaftor has a treatment effect on endothelial barrier function in the *S. pneumoniae* infected lung.

FIG. 7. Group data show that CFTR modulators reduce lung endothelial permeability after stimulation with plasma from patients with severe COVID-19 in in vitro experiments.

(A) Reduced transendothelial electrical resistance of human pulmonary microvascular endothelial cells (HPMECs) after stimulation with plasma from patients with severe COVID-19. Pre-treatment with Ivacaftor confers a protective effect on HPMECs transendothelial electrical resistance as a measure of endothelial barrier function.

(B) Reduced transendothelial electrical resistance of human pulmonary microvascular endothelial cells (HPMECs) after stimulation with plasma from patients with severe COVID-19. Pre-treatment with Lumacaftor confers a protective effect on HPMECs transendothelial electrical resistance as a measure of endothelial barrier function.

(C) Stimulation with plasma from patients with severe COVID-19 reduced CFTR expression on HPMECs and pre-treatment with Ivacaftor rescued the CFTR expression after stimulation with plasma from patients with severe COVID-19. Data are mean±SEM, *p<0.05 versus control; #p<0.05 versus COVID-19; n=3-5 each.

EXAMPLES

Example 1: Effect of Ivacaftor and Lumacaftor in Pneumolysin Treated HPMECs on Cell Permeability and CFTR Expression (In Vitro Experiments)

The effect of two CFTR modulators, the CFTR potentiator Ivacaftor and the CFTR corrector Lumacaftor, has been assessed in vitro in human pulmonary microvascular endothelial cells (HPMECs) stimulated with pneumolysin (PLY) toxin from *S. pneumoniae.*

HPMECs were purchased from PromoCell and cultured in microvascular endothelial cell growth medium, endothelial cell growth supplement, and penicillin-streptomycin at 37° C. under 5% $CO_2$. Experiments were performed using cells up to the tenth passage. Cells were grown to a confluent monolayer and permeability of the endothelial monolayer was assessed by measuring the transendothelial electrical resistance as follows:

The transendothelial electrical resistance is measured in real-time by Electric Cell-Substrate Impedance Sensing (ECIS) of the cell monolayer as a measure of endothelial permeability. HPMECs were grown in 8 wells ECIS plates to confluence. Confluent cells were pretreated with 10 μmol/L Ivacaftor (Cayman chemical) or 5 μmol/L Lumacaftor (TargetMol) for 24 hours and then stimulated with 0.25 μg/ml pneumolysin (toxin from *S. pneumoniae*). The resistance of the endothelial cell monolayer was measured as a parameter for cells permeability. As positive control, cells were stimulated with pneumolysin alone (in the absence of CFTR modulators). Non-treated cells served as negative control.

Permeability of endothelial cells has been additionally assessed by measuring the endothelial calcium concentration as follows: Increases in the endothelial calcium concentration represent a key mechanism that underlies the increase endothelial cell permeability. Increased endothelial calcium leads to contraction of the cells and increase gap formation between endothelial cells that lead to increased permeability. In this measurement, HPMECs were cultured in channel slides to confluence. The confluent cells were incubated for 30 min with Hanks Balanced Salt Solution containing 5% fetal bovine serum (FBS) and 10 μmol/L of the calcium sensitive dye fura-2-acetoxymethyl ester (fura-2AM) dissolved in Pluronic F-127 (20% solution in DMSO). The cells were then mounted in a heated chamber at 37° C. and perfused with Hank's salt solution containing 5% FBS with 10 μmol/L Ivacaftor (Cayman chemical) for 30 min followed by PLY (0.25 μg/ml) stimulation for 30 min. Fura-2 fluorescence was excited by monochromatic illumination at wavelength 340 and 380 nm. After background correction, the 340/380 ratio was calculated using TillVision 4.0 software (Till Photonics Germany) as a measure of endothelial calcium concentration. As positive or negative controls, cells were stimulated with only pneumolysin or non-treated cells were used, respectively.

CFTR expression in endothelial cells was assessed by Western blotting. HPMECs were grown in 6 well plates to confluence. The confluent cells were pretreated with 10 μmol/L Ivacaftor (Cayman chemical) for 24 hours and the next day were stimulated with 0.25 μg/ml PLY for 18 h. Cells were lysed in RIPA buffer and protein concentration was measured by BCA assay and samples were stored at −80° C. or immediately analysed by western blot. Western blots were performed using 7.5% gel. After gel transfer, the blot membrane was incubated for 1 h in 5% milk diluted in tris buffer saline with tween 0.1% (TBS-T) followed by incubation for 24 h with CFTR antibody as the primary antibody diluted 1:500 in TBS-T. The next day, the membrane was incubated for 2 h in donkey anti rabbit as the secondary antibody diluted 1:10000 in TBS-T.

FIGS. 1A and B show a reduced resistance of HPME cells after stimulation with pneumolysin indicating an increased permeability of these cells when compared to the control cells. Pre-treatment with Ivacaftor (FIG. 1A) or Lumacaftor (FIG. 1B) shows less reduced resistance of HPME cells after stimulation with pneumolysin indicating a protective effect of these compounds on endothelial permeability.

FIG. 1C shows a respective Western Blot. CFTR expression is reduced in HPME cells after stimulation with pneumolysin versus control cells. Pre-treatment with Ivacaftor shows CFTR expression comparable to control cells. Hence, Ivacaftor rescued the CFTR expression after PLY stimulation.

FIG. 2 shows an increased endothelial calcium concentration ($[Ca2^+]_i$) in HPME cells after stimulation with pneumolysin indicating an increased permeability of these cells when compared to control cells. Pre-treatment with Ivacaftor shows a lesser increase in $[Ca2^+]$; in HPME cells after stimulation with pneumolysin indicating a protective effect of Ivacaftor on endothelial permeability.

The data show that both CFTR modulators Ivacaftor and Lumacaftor confer protective effects against HPMECs permeability after stimulation with pneumolysin toxin.

Example 2: Effect of Ivacaftor on Lung Endothelial Permeability in Experimental Pneumolysin Induced Pulmonary Barrier Failure in Isolated Perfused Mouse Lungs The effect of Ivacaftor has been assessed ex vivo in isolated perfused mouse lungs upon stimulation with PLY (0.25 μg/ml) by determination of the lung weight gain.

The mice were anesthetized by intraperitoneal injection of ketamine (100 mg/kg BW) and xylazine (20 mg/kg BW). A tracheal tube was inserted into the trachea and the chest was opened by median sternotomy. Heparin (20 IU) was injected into the right ventricle to prevent blood coagulation. The main pulmonary artery and left ventricle were cannulated. Trachea, lung and heart were removed en bloc and connected to an isolated pulmonary perfusion system. The lungs were continuously perfused with Hanks Balanced Salt Solution (HBSS) containing 5% FBS at a rate of 1 mL/min. Lung weight is continuously monitored as a measure for the formation of pulmonary edema.

Mice lungs were pretreated with Ivacaftor (final concentration of 10 μmol/L) and then stimulated with pneumolysin toxin from *S. pneumoniae* (final concentration of 0.25 micro g/ml).

As positive and negative controls, mouse lungs were stimulated with pneumolysin alone or non-treated mouse lungs were used, respectively.

FIG. 3 shows that pneumolysin stimulation results in lung weight gain compared to non-treated lungs. Ivacaftor pretreatment reduced this effect significantly. These data show that lung endothelial permeability and edema formation as evident by increased lung weight gain upon stimulation with pneumolysin is reduced by Ivacaftor pre-treatment.

Example 3: Effect of Ivacaftor in *S. pneumoniae* Infected Mice on Lung Edema Formation and on Pulmonary Immune Response (In Vivo Experiments)

The effect of Ivacaftor was assessed in vivo in mouse lungs following infection with *S. pneumoniae* by determination of endogenous mouse serum albumin and exogenous human serum albumin in the bronchoalveolar lavage fluid (BALF) and in plasma.

Mice were purchased from Charles River (Germany) and housed in isolated ventilated cages under specific pathogen free (SPF) conditions with a 12 h light dark cycle and free access to food and water. For infection mice were anesthetized with ketamine and xylazine and transnasally inoculated with $5\times10^6$ colony-forming units (CFU) of *S. pneumoniae* (NCTC7978) in 20 μL of sterile PBS. Non-infected control mice received 20 μL of sterile PBS. Mice were pretreated with Ivacaftor (Cayman chemical; 2 mg/kg in 100 μL intraperitoneally; i.p.) or as a control with solvent 24 h before infection, and further at time point of infection and 12 h, 24 h, 36 h and 47 h after infection. At the same time points body weight and rectal temperature were measured.

Accordingly, the following experimental groups were included:

- Mice non-infected and treated with solvent
- Mice non-infected and treated with Ivacaftor
- Mice infected with *S. pneumoniae* and treated with solvent
- Mice infected with *S. pneumoniae* and treated with Ivacaftor Forty-eight hours postinfection (p.i.), mice were anesthetized (ketamine/xylazine) and exsanguinated. Subsequently, lungs were flushed, bronchoalveolar lavage (BAL) was performed and lung tissue was dissected and frozen in liquid nitrogen.

The experimental protocol of the in vivo experiments is shown in FIG. 4A.

Endogenous mouse serum albumin (MSA) in the bronchoalveolar lavage fluid (BALF) and blood plasma was quantified by ELISA (Bethyl Laboratories, Montgomery, TX, USA) and the BALF/plasma ratio was calculated as a marker of pulmonary vascular permeability.

Exogenous human serum albumin (HSA; 1 mg/75 μl) was intravenously injected 1 h before lung preparation and BAL. HSA concentration in BALF and plasma was measured by ELISA (Bethyl, Montgomery, TX, USA) and the HSA BALF/plasma-ratio was calculated as marker of pulmonary vascular permeability.

CFTR expression in mice was assessed by Western blotting as described in Example 1. The number of total leukocytes, polymorphonuclear leukocytes (PMN), and inflammatory macrophages in the bronchoalveolar lavage fluid (BALF) was measured by fluorescence-activated cell sorting (FACSCanto II; BD Biosciences) using forward-vs. side-scatter characteristics for cell gating, and subsequent differentiation by fluorescence labeling. To this end, BAL cells were preincubated with blocking antibody and stained with anti-CD45, anti-CD11c, anti-CD11b, anti-F4/80, anti-Ly6G, anti-Ly6C, anti-Siglec F and anti-MHCII antibodies. Cells were measured and analyzed with FACS Canto II (BD) and FACSDiva and FlowJo-software. Cell numbers were calculated using CountBright Absolute Counting Beads (ThermoFisher Scientific).

FIGS. 4B and C show that mice infected with *S. pneumoniae* have an increased permeability of the endothelial/epithelial barrier compared to lungs of non-infected mice evident as increased leak of endogenous murine serum albumin and exogenous human serum albumin from the plasma into the alveolar space from where it was retrieved by broncho-alveolar lavage. Ivacaftor pre-treatment reduced protein leakage into the lung. Hence, lung protein permeability upon infection with *S. pneumoniae* is reduced by Ivacaftor pre-treatment.

Figure 1A:
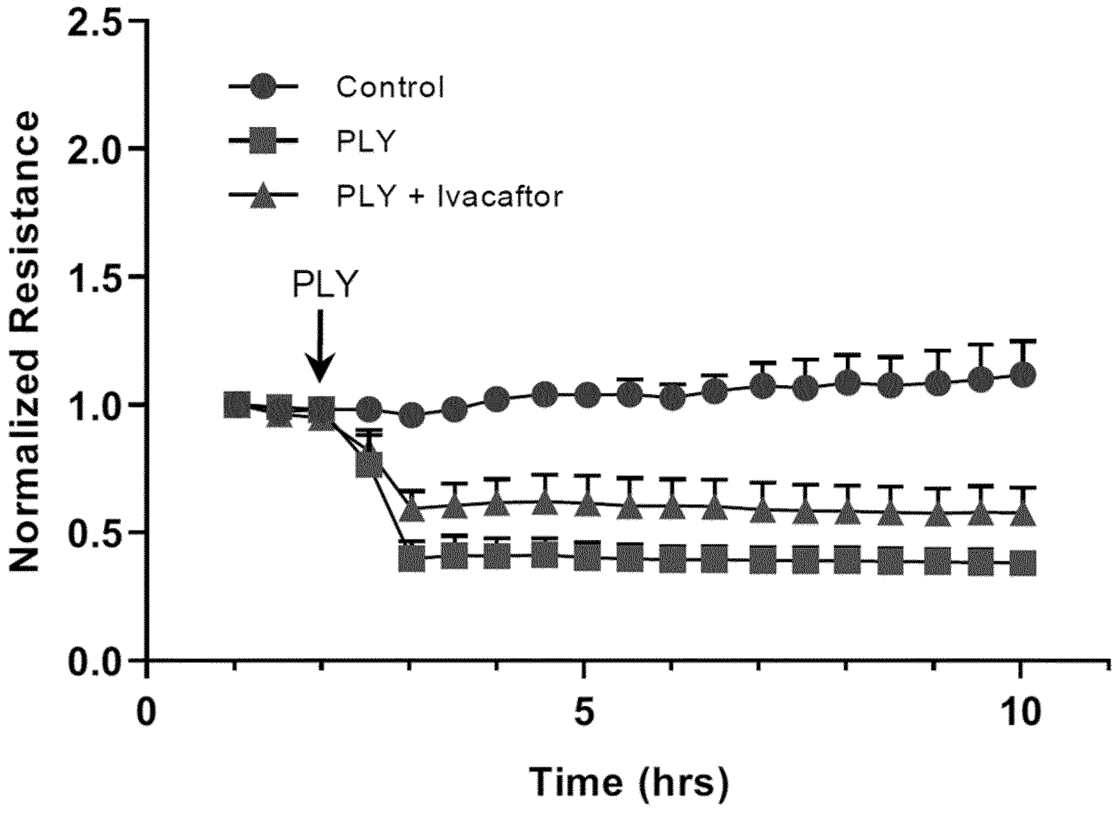
Figure 1B:
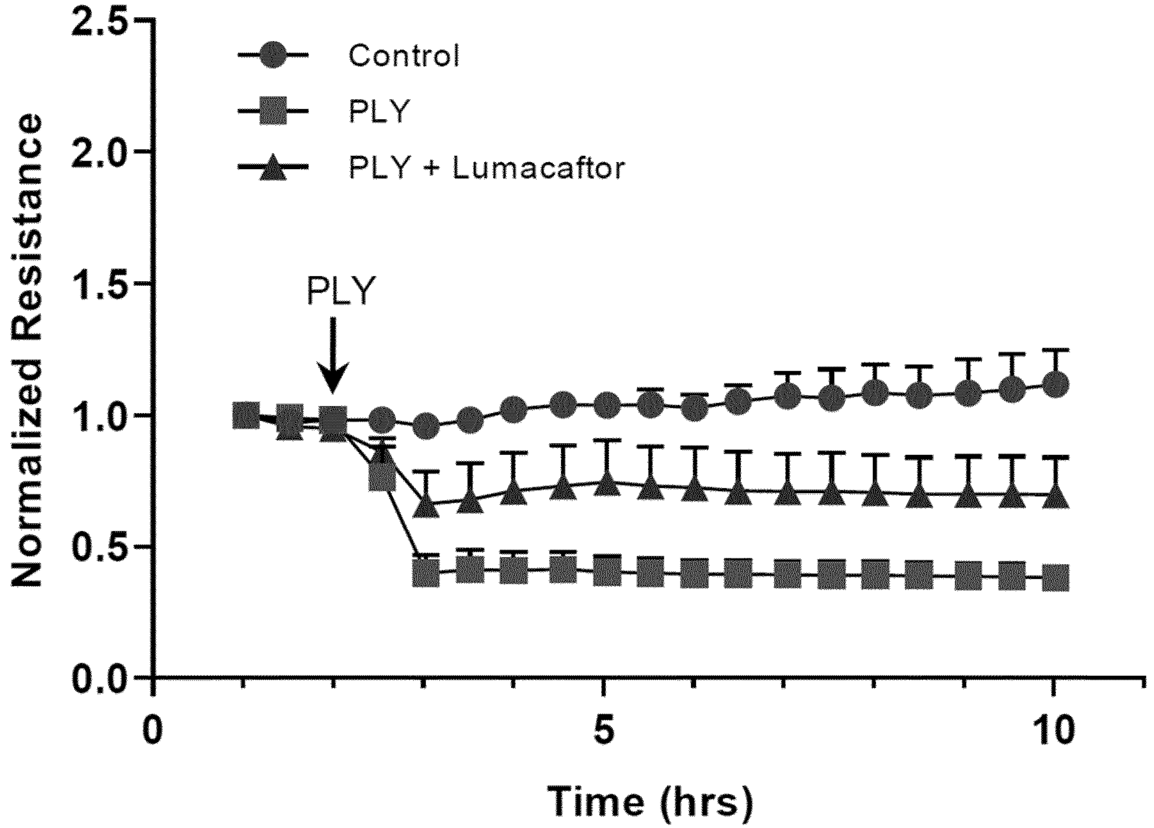
Figure 1C:
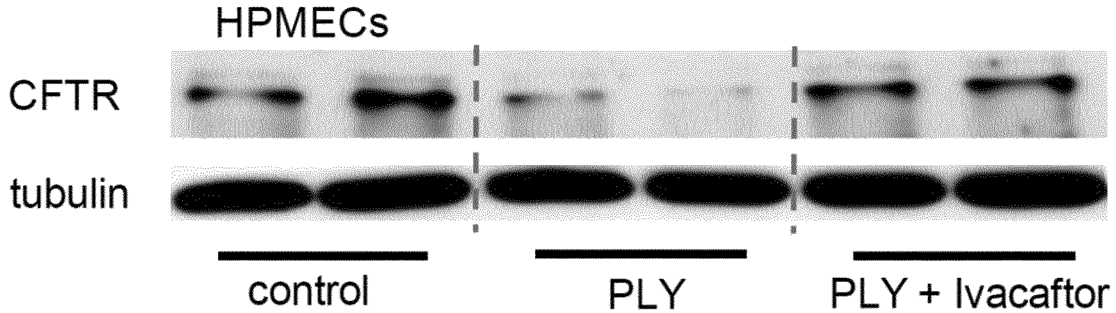
Figure 2:
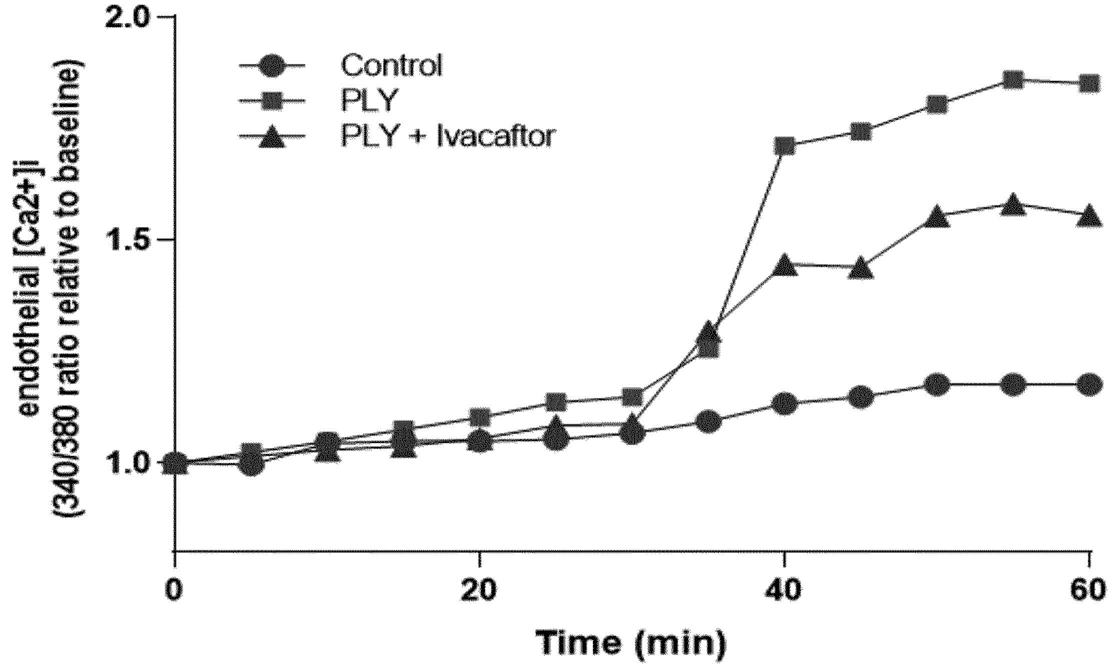
Figure 3:
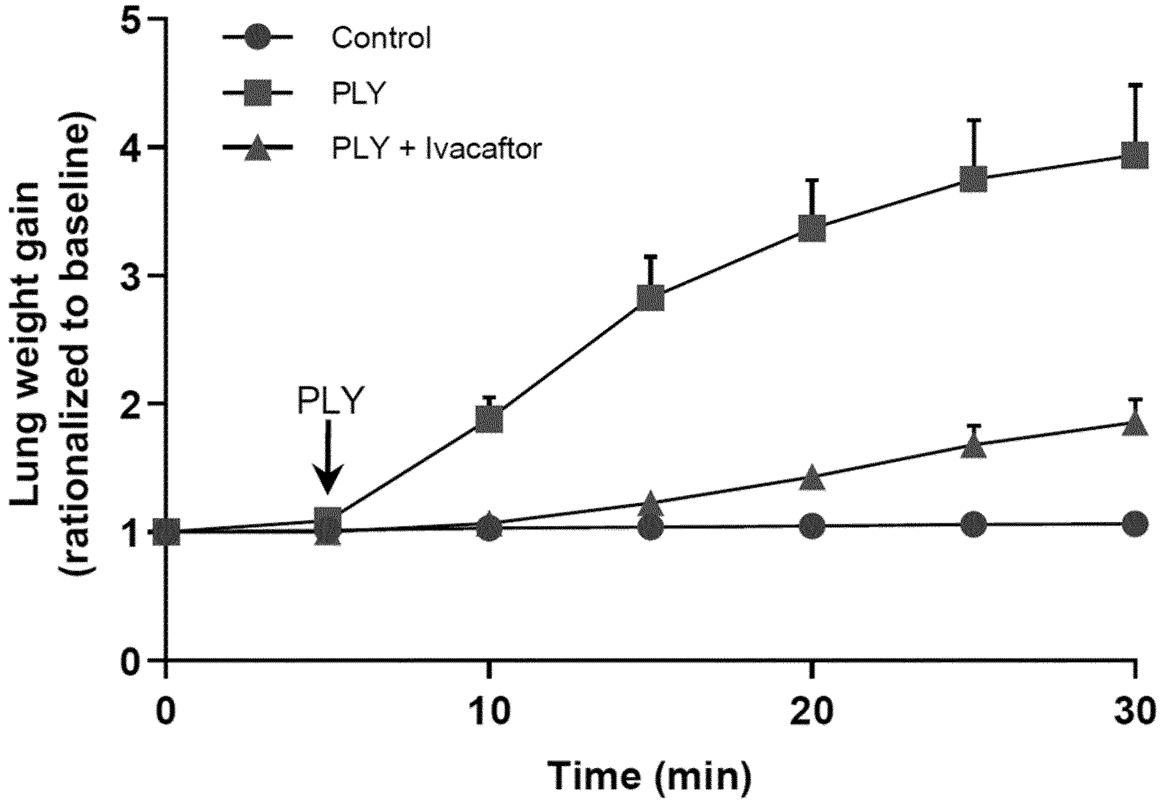
Figure 4A:
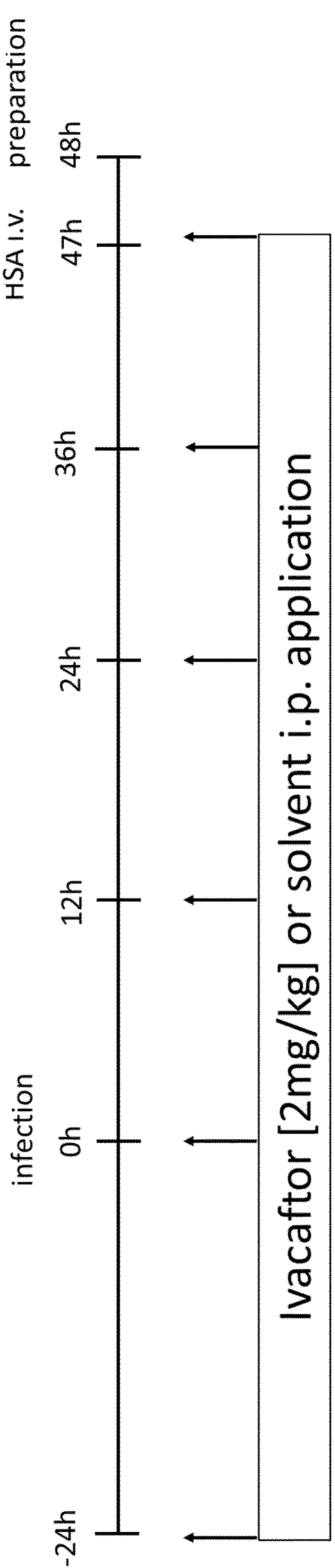
FIG. 4D shows that Ivacaftor pre-treatment increased survival rate in *S. pneumoniae* infected mice.
FIG. 4E shows that mice infected with *S. pneumoniae* show a reduced CFTR expression compared to non-infected mice. Ivacaftor pre-treatment stabilized expression of CFTR.
Figure 4B:
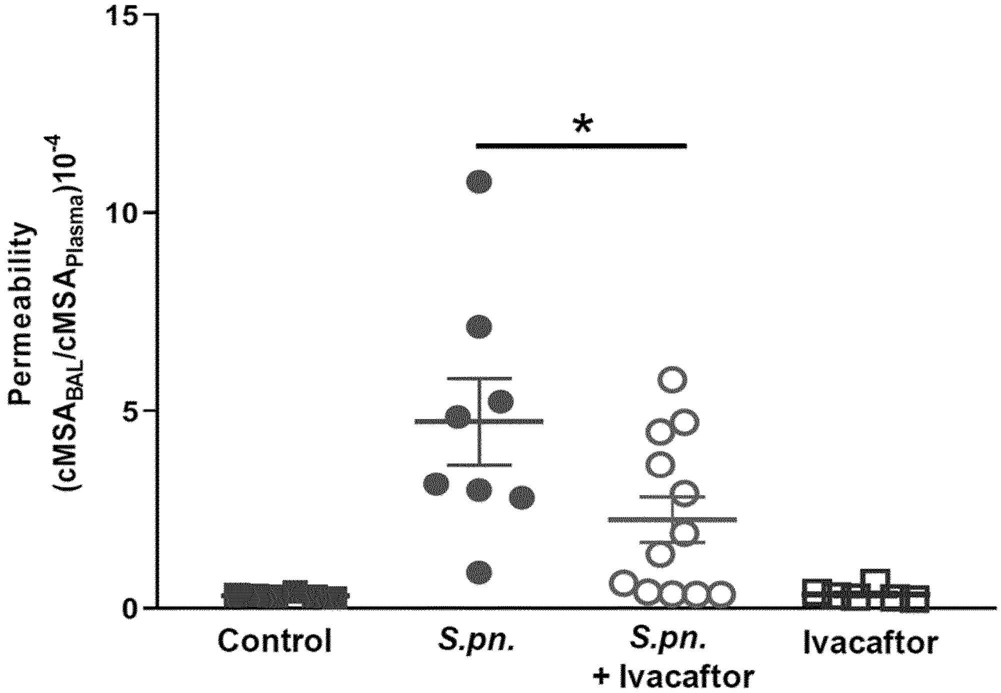
Figure 4C:
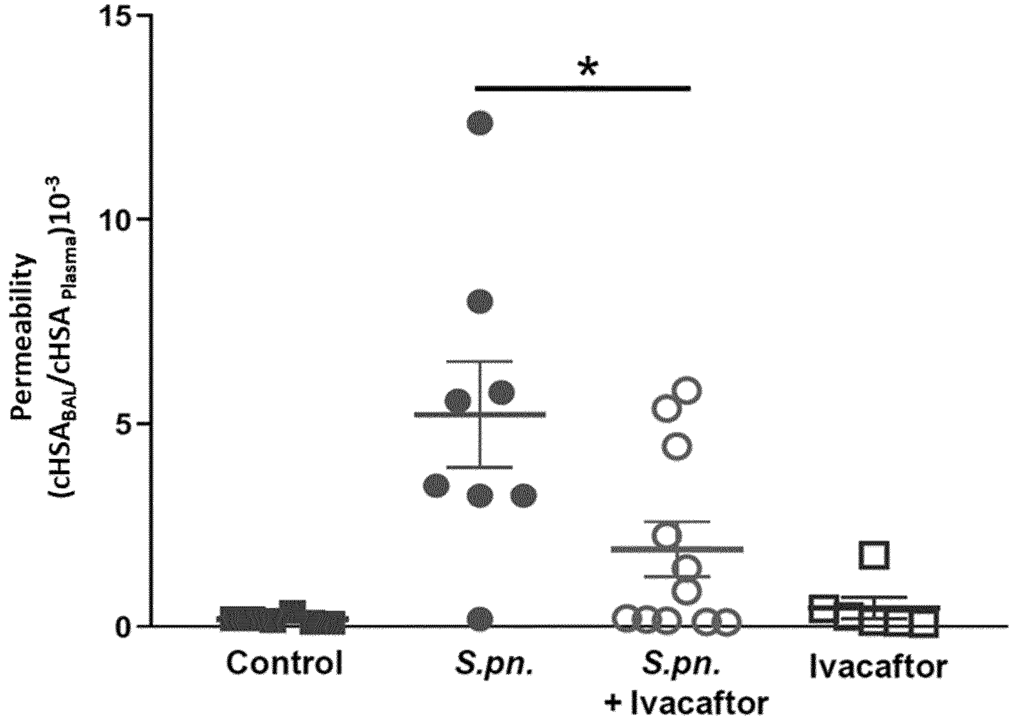
Figure 4D:
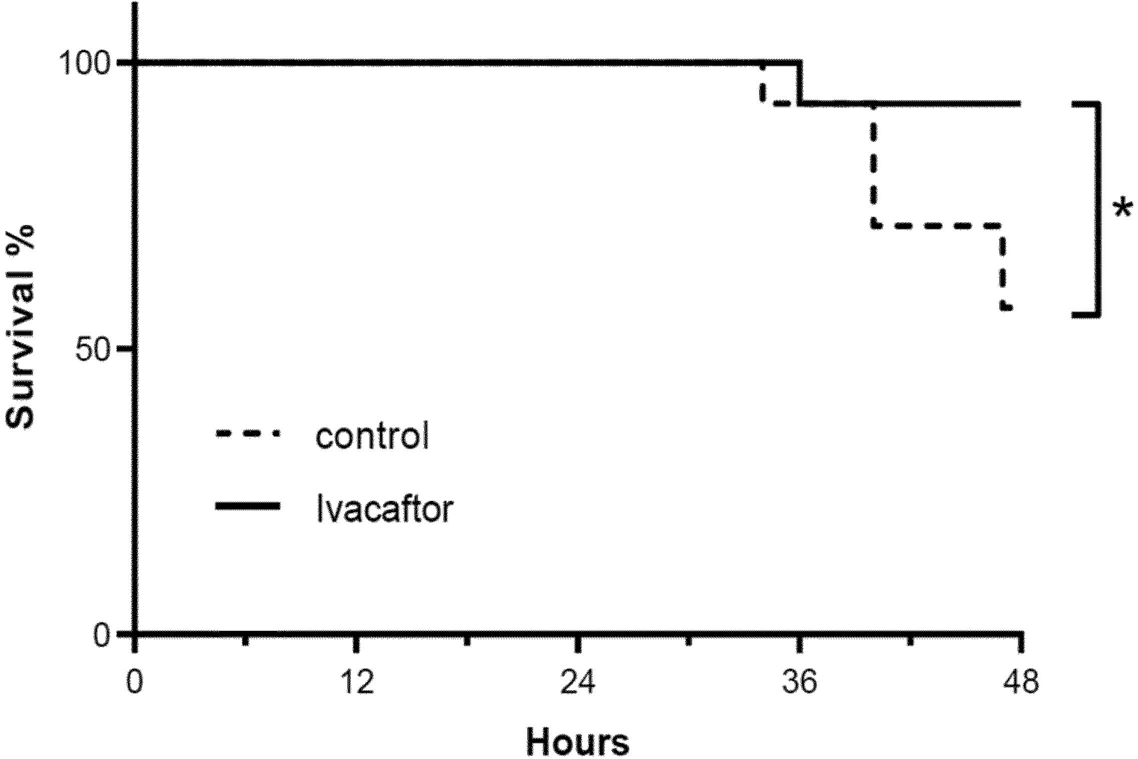
Figure 4E:
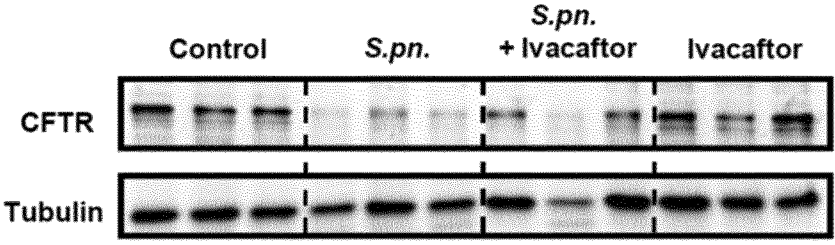
Figure 4E:
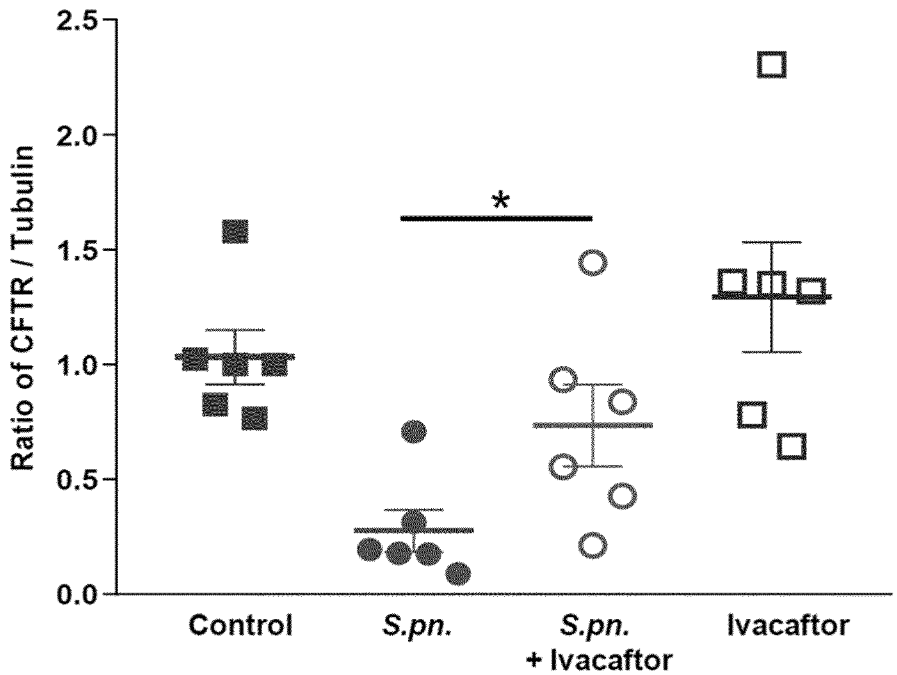
Figure 5A:
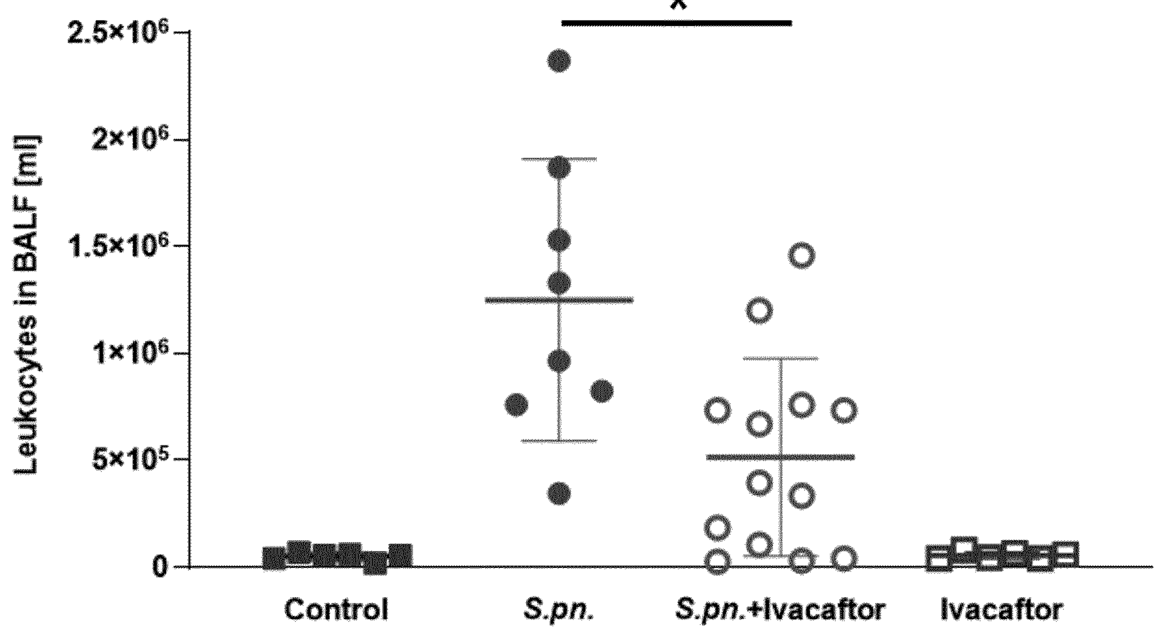
Figure 5B:
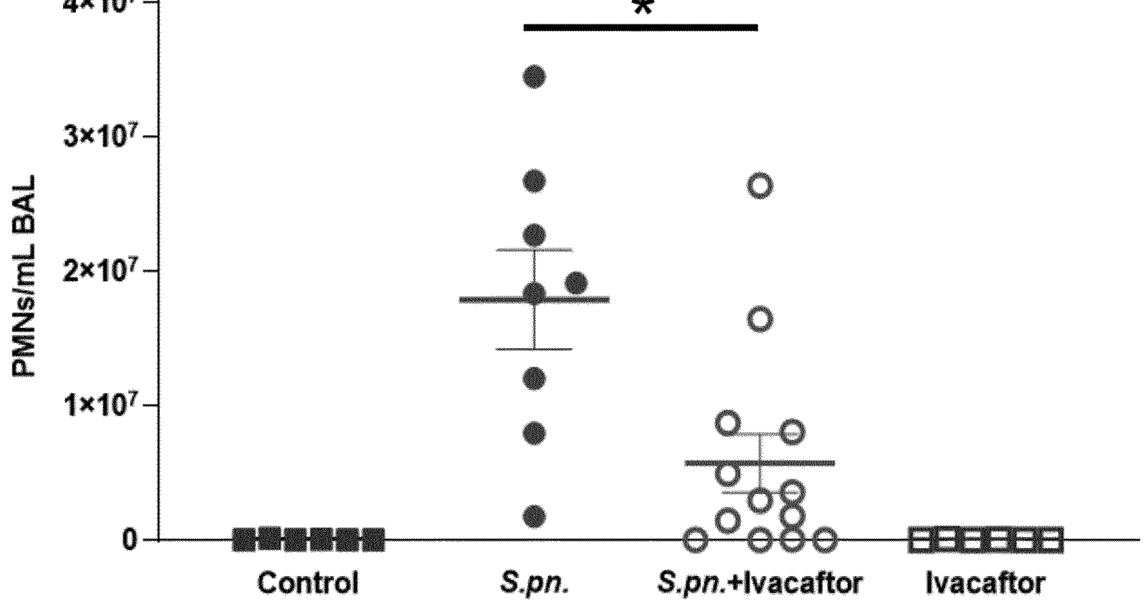
Figure 5C:
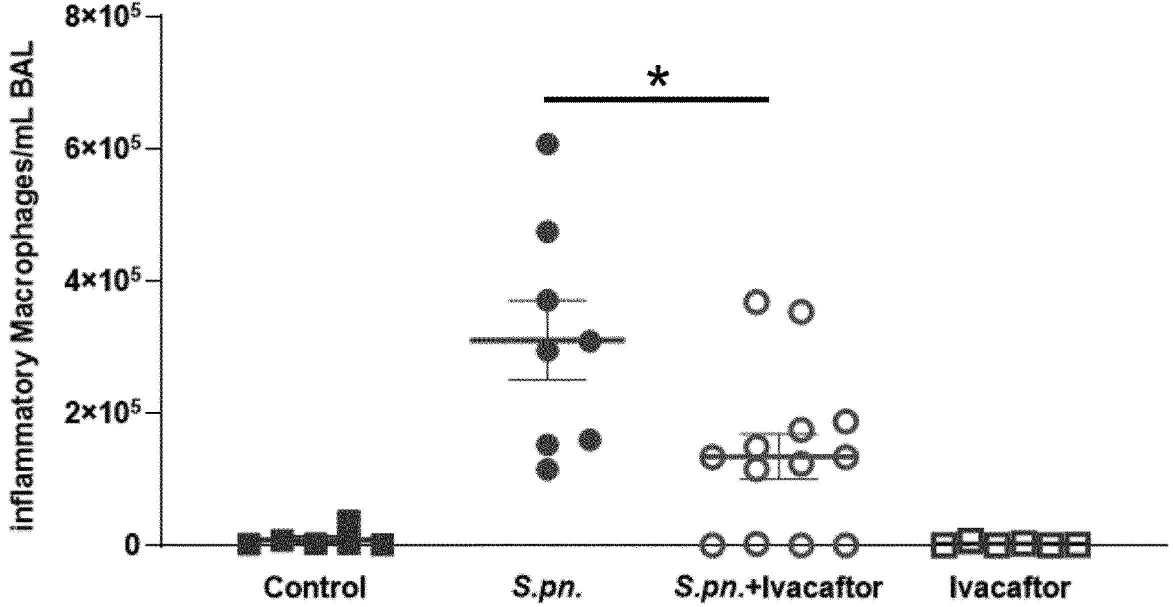

FIGS. 5A-C reveal that mice infected with *S. pneumoniae* show an increased accumulation of (A) leukocytes, (B) polymorphonuclear leukocytes (PMN) and (C) inflammatory macrophages in BALF compared to non-infected mice. Ivacaftor pre-treatment decreased the levels of all three inflammatory cell subsets in the BALF, demonstrating that the immigration of immune cells across the endothelial and epithelial barrier into the alveolar space following infection with *S. pneumoniae* is reduced by Ivacaftor pre-treatment.

In summary, the experimental data show that Lumacaftor and Ivacaftor pre-treatment have protective effects on endothelial barrier function in vitro, and on lung barrier function, i.e. epithelial and endothelial barrier function, in vivo.

Example 4: Effect of Ivacaftor in *S. pneumoniae* Infected Mice on Lung Edema Formation and on Pulmonary Immune Response (In Vivo Experiments—Post Treatment)

The effect of Ivacaftor was assessed in vivo in mouse lungs following infection with *S. pneumoniae* by determination of endogenous mouse serum albumin and exogenous human serum albumin in the bronchoalveolar lavage fluid (BALF) and in plasma.

Mice were purchased from Charles River (Germany) and housed in isolated ventilated cages under specific pathogen free (SPF) conditions with a 12 h light dark cycle and free access to food and water. For infection mice were anesthetized with ketamine and xylazine and transnasally inoculated with $5\times10^6$ colony-forming units (CFU) of *S. pneumoniae* (NCTC7978) in 20 UL of sterile PBS. Non-infected control mice received 20 μL of sterile PBS.

Mice were treated with Ivacaftor 6 hours post-infection (Cayman chemical; 2 mg/kg in 100 μL intraperitoneally; i.p.) or as a control with solvent 6 hours post infection, and further at time point of infection and 12 h, 24 h and 36 h after infection. At the same time points body weight and rectal temperature were measured.

Accordingly, the following experimental groups were included:

- Mice non-infected and post-treated with solvent
- Mice non-infected and post-treated with Ivacaftor
- Mice infected with *S. pneumoniae* and post-treated with solvent
- Mice infected with *S. pneumoniae* and post-treated with Ivacaftor Fourty-eight hours postinfection (p.i.), mice were anesthetized (ketamine/xylazine) and exsanguinated. Subsequently, lungs were flushed, bronchoalveolar lavage (BAL) was performed and lung tissue was dissected and frozen in liquid nitrogen.

Figure 6A:
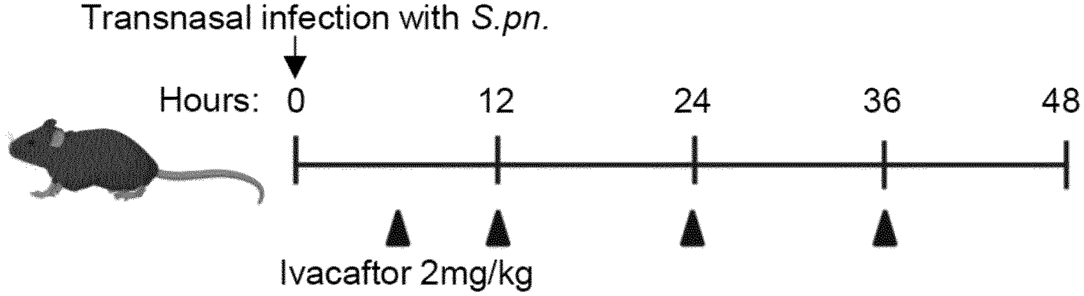

The experimental protocol of the in vivo experiments—post treatment—is shown in FIG. 6A.

Endogenous mouse serum albumin (MSA) in the bronchoalveolar lavage fluid (BALF) and blood plasma was quantified by ELISA (Bethyl Laboratories, Montgomery, TX, USA) and the BALF/plasma ratio was calculated as a marker of pulmonary vascular permeability.

Exogenous human serum albumin (HSA; 1 mg/75 μl) was intravenously injected 1 h before lung preparation and BAL. HSA concentration in BALF and plasma was measured by ELISA (Bethyl, Montgomery, TX, USA) and the HSA BALF/plasma-ratio was calculated as marker of pulmonary vascular permeability.

Figure 6B:
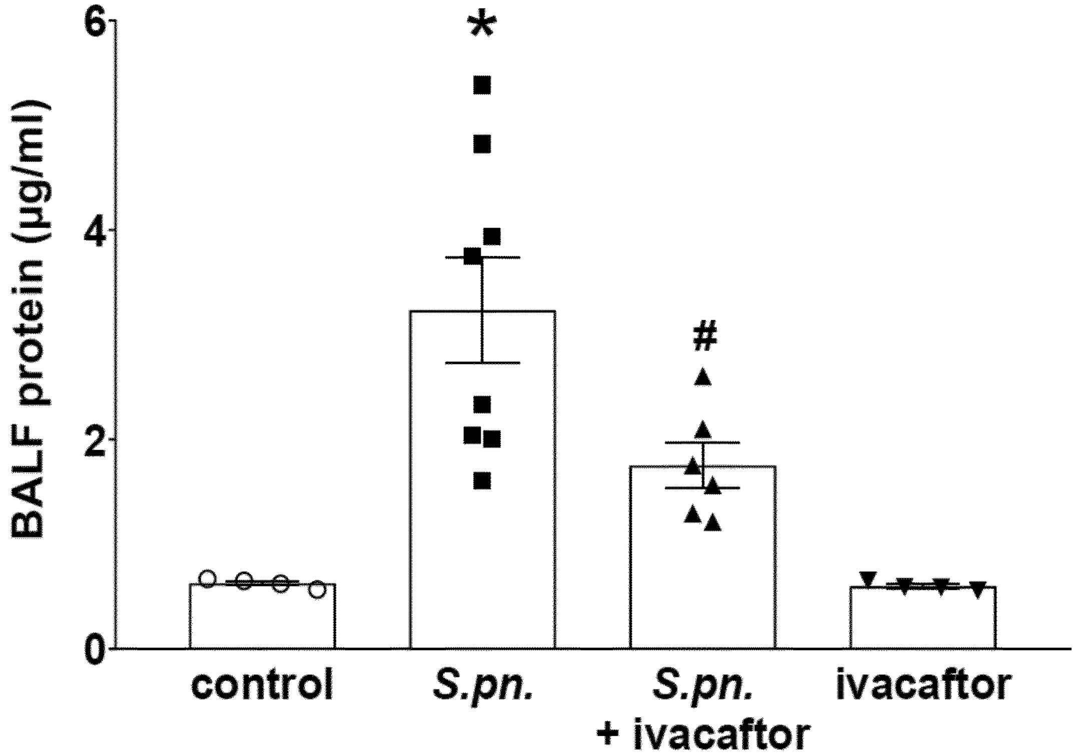
Figure 6C:
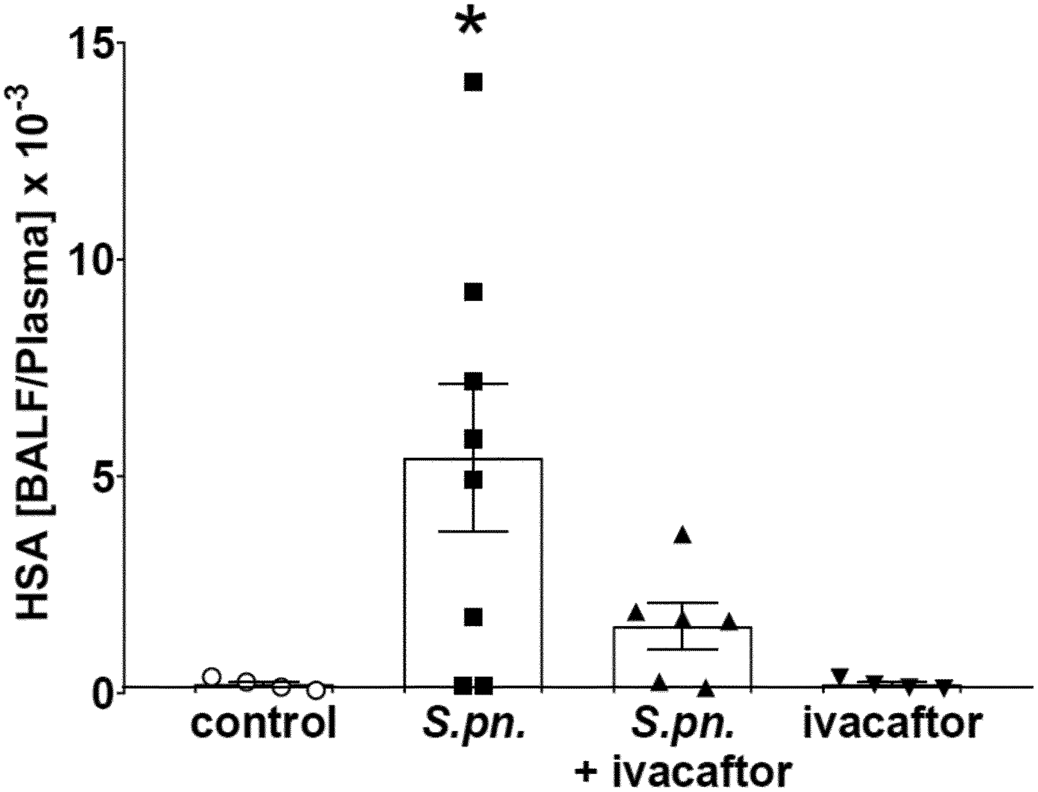

FIGS. 6B and 6C show that mice infected with *S. pneumoniae* have an increased permeability of the endothelial/epithelial barrier compared to lungs of non-infected mice evident as increased leak of endogenous murine serum albumin and exogenous human serum albumin from the plasma into the alveolar space from where it was retrieved by broncho-alveolar lavage. Ivacaftor pre-treatment reduced protein leakage into the lung. Hence, lung protein permeability upon infection with *S. pneumoniae* is reduced by Ivacaftor post-treatment.

In summary, the experimental data of Example 4 shows that Ivacaftor post-treatment has protective effects on lung alveolo-capillary barrier function, i.e. epithelial and endothelial barrier function, in vivo.

Example 5: Effect of Ivacaftor and Lumacaftor on Endothelial Permeability and CFTR Expression (In Vitro Experiments) in HPMECs Treated with Plasma from Patients with Severe COVID-19

The effect of two CFTR modulators, the CFTR potentiator Ivacaftor and the CFTR corrector Lumacaftor, has been assessed in vitro in human pulmonary microvascular endothelial cells (HPMECs) stimulated with plasma from patients with severe COVID-19.

HPMECs were purchased from PromoCell and cultured in microvascular endothelial cell growth medium, endothelial cell growth supplement, and penicillin-streptomycin at 37° C. under 5% $CO_2$. Experiments were performed using cells up to the tenth passage. Cells were grown to a confluent monolayer and permeability of the endothelial monolayer was assessed by measuring the transendothelial electrical resistance as follows:

The transendothelial electrical resistance is measured in real-time by Electric Cell-Substrate Impedance Sensing (ECIS) of the cell monolayer as a measure of endothelial permeability. HPMECs were grown in 8 wells ECIS plates to confluence. Confluent cells were pretreated with 10 μmol/L Ivacaftor (Cayman chemical) or 5 μmol/L Lumacaftor (TargetMol) for 24 hours and then stimulated with plasma from COVID-19 patients or healthy donors for 24 h as negative control. As positive control, cells were stimulated with plasma from COVID-19 patients alone (in the absence of CFTR modulators).

Citrate plasma was sampled as part of the prospective observational Pa-COVID-19 cohort study (ethics approval EA2/066/20) in 8 patients with severe disease (high flow 02 or intubated and mechanically ventilated; WHO severity score: 5-7). Plasma from 8 healthy donors (ethics approval EA2/075/15) served as control. Plasma samples were diluted to 10% (v/v) for transendothelial electrical resistance measurement as a parameter for endothelial cell permeability.

CFTR expression in endothelial cells was assessed by Western blotting. HPMECs were grown in 6 well plates to confluence. The confluent cells were pretreated with 10 μmol/L Ivacaftor (Cayman chemical) for 24 hours and the next day were stimulated with the above described plasma from COVID-19 patients or healthy donors for 24 h. As positive control, cells were stimulated with the plasma from COVID-19 patients alone (in the absence of CFTR modulators). Plasma samples were diluted to 20% (v/v) for CFTR immunoblotting.

Cells were lysed in RIPA buffer and protein concentration was measured by BCA assay and samples were stored at −80° C. or immediately analysed by Western blot. Western blots were performed using 7.5% gel. After gel transfer, the blot membrane was incubated for 1 h in 5% milk diluted in tris buffer saline with tween 0.1% (TBS-T) followed by incubation for 24 h with CFTR antibody as the primary antibody diluted 1:500 in TBS-T. The next day, the membrane was incubated for 2 h in donkey anti rabbit as the secondary antibody diluted 1:10000 in TBS-T.

Figure 7A:
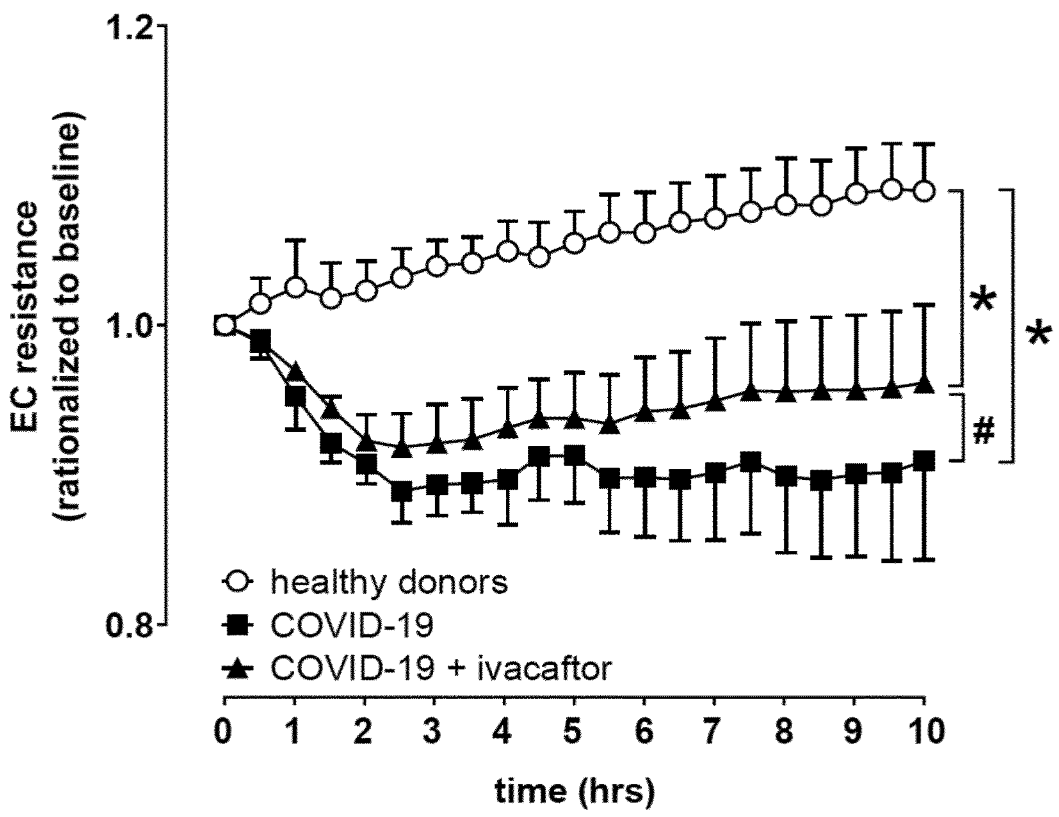
Figure 7B:
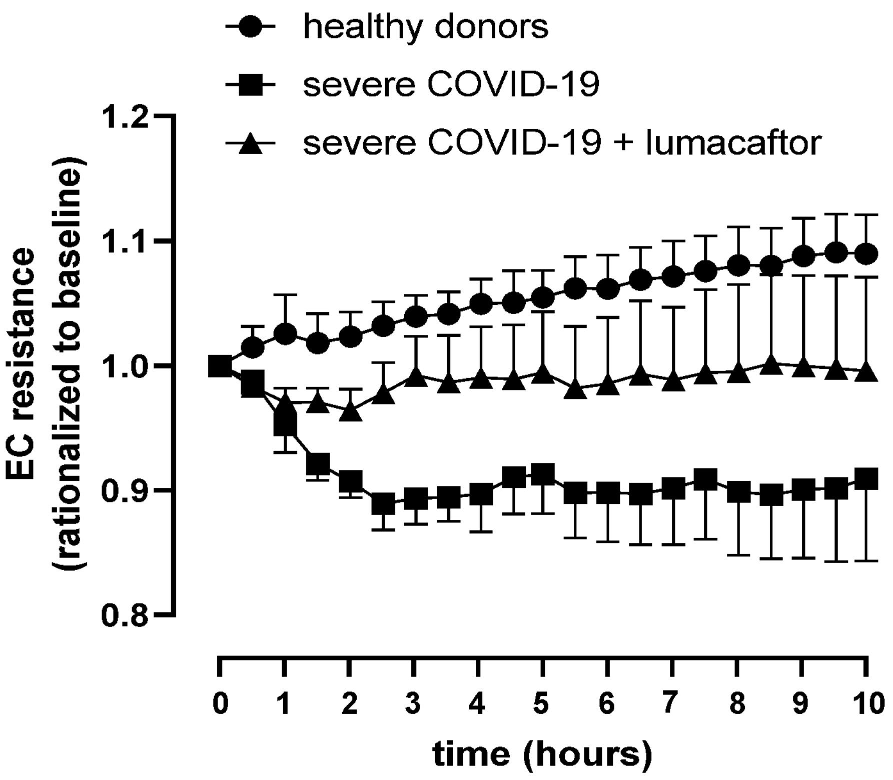

FIGS. 7A and B show a reduced transendothelial electrical resistance of HPME cells after stimulation with plasma from COVID-19 patients indicating an increased permeability of these cells when compared to the control cells. Pre-treatment with Ivacaftor (FIG. 7A) or Lumacaftor (FIG. 7B) shows less reduced transendothelial electrical resistance of HPME cells after stimulation with plasma from COVID-19 patients indicating a protective effect of these compounds on endothelial permeability.

Figure 7C:
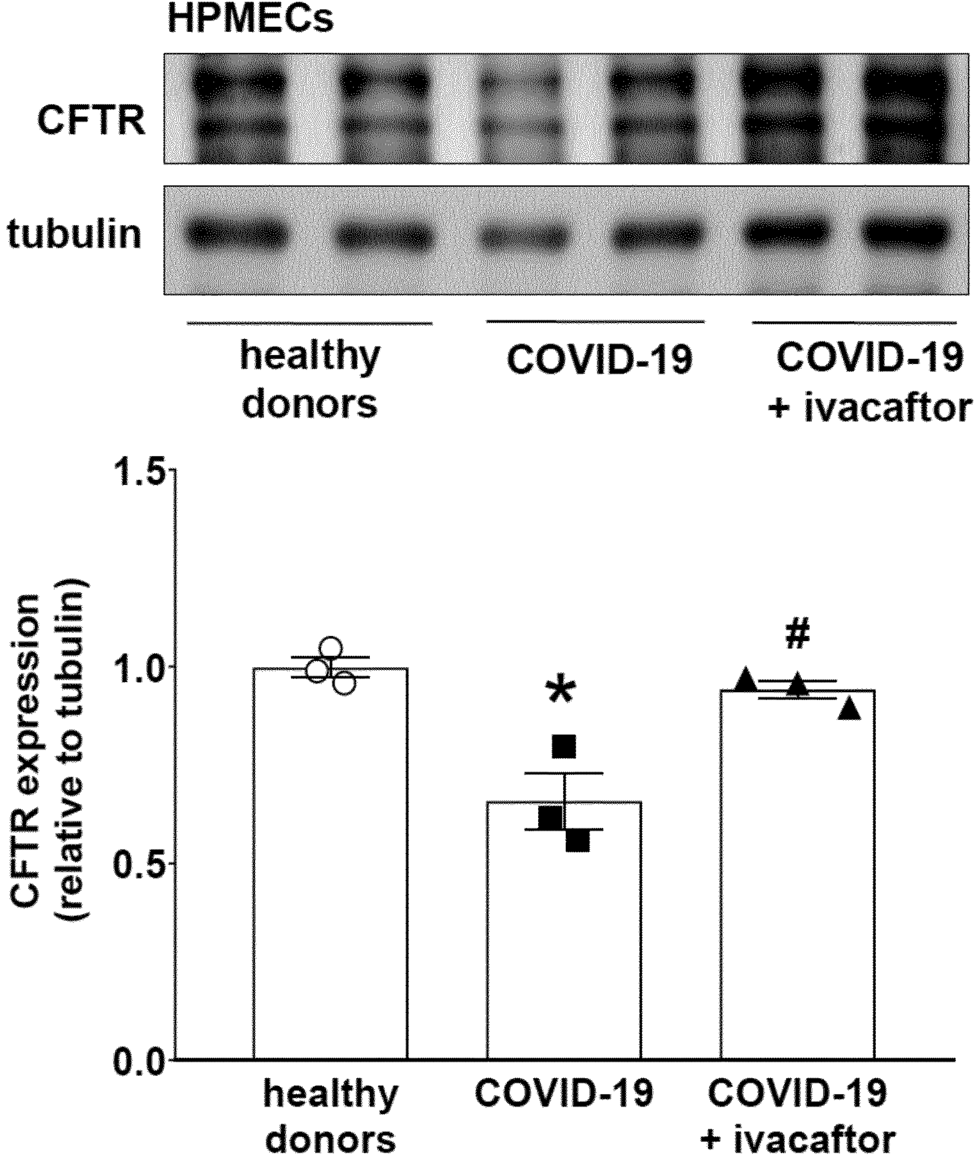

FIG. 7C shows a respective Western Blot together with a densitometric quantification of three independent experiments. CFTR expression is reduced in HPME cells after stimulation with plasma from COVID-19 patients versus control cells stimulated with plasma from healthy donors. Pre-treatment with Ivacaftor shows CFTR expression comparable to control cells. Hence, Ivacaftor rescued the CFTR expression after stimulation with plasma from COVID-19 patients.

In summary, the experimental data of Example 5 shows that Lumacaftor and Ivacaftor pre-treatment have protective effects on endothelial barrier function for COVID-19 patients in vitro.

The invention claimed is:

1. A method of preventing and/or treating a disease involving endothelial and/or epithelial barrier dysfunctions, the method comprising administering a CFTR modulator, wherein the disease does not comprise cystic fibrosis;

wherein the CFTR modulator is a CFTR potentiator, a CFTR corrector, or a CFTR amplifier, wherein the CFTR potentiator is a compound selected from Ivacaftor, GLPG2451, GLPG1837, QBW251, PTI-808, FDL176 or a deuterated compound or pharmaceutically acceptable salt thereof;

wherein the CFTR corrector is a compound selected from Lumacaftor, Tezacaftor, Elexacaftor, Bamocaftor, Bamocaftor potassium, Posenacaftor, Cavosonstat, GLPG2222, GLPG2737, or a deuterated compound or pharmaceutically acceptable salt thereof; and wherein the CFTR amplifier is a compound selected from Nesolicaftor and PTI-CH, or a deuterated compound or pharmaceutically acceptable salt thereof.

2. The method according to claim 1, wherein the disease involves a permeability-type edema.

3. The method according to claim 1, wherein the disease involves a pulmonary permeability-type edema.

4. The method according to claim 1, wherein the disease is an acute disease.

5. The method according to claim 1, wherein the disease is an inflammatory disease.

6. The method according to claim 1, wherein the disease is an infectious disease.

7. The method according to claim 1, wherein the disease is a pulmonary disease, systemic inflammatory response syndrome, COVID-19 or sepsis.

8. The method according to claim 7, wherein the pulmonary disease is acute respiratory distress syndrome, ventilator induced lung injury, transfusion-associated acute lung injury or pneumonia including COVID-19 associated pneumonia.

9. The method according to claim 1, wherein the modulator is a compound of Formula I or Formula IV:

Formula I

Formula IV

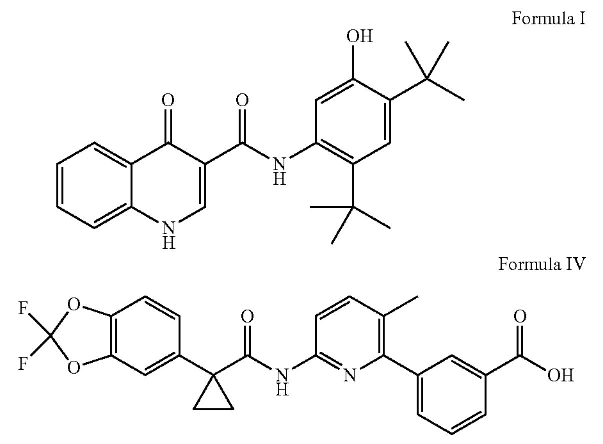

or a deuterated compound of Formula I or Formula IV, or a pharmaceutically acceptable salt thereof.

10. The method according to claim 9, wherein the CFTR modulator is the deuterated compound of Formula I or Formula IV or a pharmaceutically acceptable salt thereof.

11. The method according to claim 9, wherein the modulator is the compound of Formula I or Formula IV, or a pharmaceutically acceptable salt thereof.

12. The method according to claim 1, wherein the CFTR modulator is used in combination with one or more further CFTR modulators.

13. A method of preventing and/or treating a disease involving endothelial and/or epithelial barrier dysfunctions, the method comprising administering a pharmaceutical composition comprising a CFTR modulator as an active ingredient, wherein the disease does not comprise cystic fibrosis;

wherein the CFTR modulator is a CFTR potentiator a CFTR corrector, or a CFTR amplifier, wherein the CFTR potentiator is a compound selected from Ivacaftor, GLPG2451, GLPG1837, QBW251, PTI-808, FDL176 or a deuterated compound or pharmaceutically acceptable salt thereof;

wherein the CFTR corrector is a compound selected from Lumacaftor, Tezacaftor, Elexacaltor, Bamocaftor, Bamocaftor potassium, Posenacaftor, Cavosonstat, GLPG2222, GLPG2737, or a deuterated compound or pharmaceutically acceptable salI thereof; and wherein the OFTR amplifier is a compound selected from Nesolicaftor and PTI-CH, or a deuterated compound or pharmaceutically acceptable salI thereof.

14. A method of preventing and/or treating a disease involving endothelial and/or epithelial barrier dysfunctions, the method comprising administering the components of a kit of parts comprising i) a CFTR modulator and ii) a further CFTR modulator wherein the disease does not comprise cystic fibrosis;

wherein the CFTR modulator is a CFTR potentiator, a CFTR corrector, or a CFTR amplifier, wherein the CFTR potentiator is a compound selected from Ivacaftor, GLPG2451, GLPG1837, QBW251, PTI-808, FDL176 or a deuterated compound or pharmaceutically acceptable salt thereof;

wherein the CFTR corrector is a compound selected from Lumacaftor, Tezacaftor, Elexacaltor, Bamocaftor, Bamocaftor potassium, Posenacaflor, Cavosonstat, GLPG2222, GLPG2737, or a deuterated compound or pharmaceutically acceptable salI thereof; and wherein the CFTR amplifier is a compound selected from Nesolicaftor and PTI-CH, or a deulerated compound or pharmaceutically acceptable salt thereof.

15. The method according to claim 1, wherein the disease involving endothelial and/or epithelial barrier dysfunction does not comprise diseases involving a hydrostatic pulmonary edema.

* * * * *